(12) United States Patent
Larsen et al.

(10) Patent No.: US 11,253,301 B2
(45) Date of Patent: Feb. 22, 2022

(54) APPARATUS AND METHOD FOR SYNDESMOSIS FIXATION

(71) Applicant: DEPUY SYNTHES PRODUCTS, INC., Raynham, MA (US)

(72) Inventors: Scott P. Larsen, West Chester, PA (US); Kevin Clancy, West Chester, PA (US); Mark Siravo, West Chester, PA (US); Glen Pierson, West Chester, PA (US); Wamis Singhatat, West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 316 days.

(21) Appl. No.: 16/528,910

(22) Filed: Aug. 1, 2019

(65) Prior Publication Data

US 2019/0350629 A1   Nov. 21, 2019

Related U.S. Application Data

(62) Division of application No. 14/457,850, filed on Aug. 12, 2014, now abandoned.

(60) Provisional application No. 61/866,347, filed on Aug. 15, 2013.

(51) Int. Cl.
| | |
|---|---|
| *A61B 17/04* | (2006.01) |
| *A61B 17/82* | (2006.01) |
| *A61B 17/80* | (2006.01) |

(52) U.S. Cl.
CPC .............. *A61B 17/82* (2013.01); *A61B 17/80* (2013.01); *A61B 2017/0403* (2013.01); *A61B 2017/044* (2013.01); *A61B 2017/0406* (2013.01); *A61B 2017/0427* (2013.01)

(58) Field of Classification Search
None
See application file for complete search history.

(56) References Cited

U.S. PATENT DOCUMENTS

| | | | |
|---|---|---|---|
| 6,368,326 B1 | 4/2002 | Dakin et al. | |
| 9,039,739 B2 | 5/2015 | Rohlinger et al. | |
| 2003/0236555 A1* | 12/2003 | Thornes | A61B 17/0401 606/232 |
| 2007/0225716 A1 | 9/2007 | Deffenbaugh et al. | |

(Continued)

FOREIGN PATENT DOCUMENTS

| | | |
|---|---|---|
| CN | 101040795 | 9/2007 |
| CN | 102933158 | 3/2013 |

(Continued)

OTHER PUBLICATIONS

International Search Report and Written Opinion (PCT/US2014/050746); dated Oct. 30, 2014.

(Continued)

*Primary Examiner* — Samuel S Hanna
(74) *Attorney, Agent, or Firm* — Dunlap Codding, P.C.

(57) ABSTRACT

A method for syndesmosis fixation including at least one suture anchor configured to be implanted into bone and at least one suture assembly configured to extend from the suture anchor and about at least a portion of a fibula when the suture anchor is implanted in a tibia on either side of a fibular notch of the tibia. The suture assembly is selectively adjustable from a non-tensioned condition to a tensioned condition to stabilize and reduce the fibula relative to the tibia.

9 Claims, 35 Drawing Sheets

(56) References Cited

U.S. PATENT DOCUMENTS

| | | |
|---|---|---|
| 2009/0088798 A1 | 4/2009 | Snyder et al. |
| 2010/0094079 A1 | 4/2010 | Inman et al. |
| 2010/0106254 A1 | 4/2010 | DelSignore |
| 2010/0211075 A1 | 8/2010 | Stone |
| 2012/0108890 A1 | 5/2012 | Evans |
| 2012/0109156 A1 | 5/2012 | Overes et al. |
| 2012/0150223 A1 | 6/2012 | Manos et al. |
| 2012/0271416 A1 | 10/2012 | Mackay |
| 2013/0030480 A1 | 1/2013 | Donate et al. |

FOREIGN PATENT DOCUMENTS

| | | |
|---|---|---|
| WO | 1999/037219 | 7/1999 |
| WO | 2007/002071 A1 | 1/2007 |

OTHER PUBLICATIONS

First Office action (CN201480045325.X), dated Nov. 3, 2017.
Provisional U.S. Appl. No. 61/683,382, filed Aug. 15, 2012 titled Bone Plate Suture Anchor.

\* cited by examiner

APPARATUS AND METHOD FOR SYNDESMOSIS FIXATION

CROSS REFERENCE TO RELATED APPLICATION

This application is a divisional of U.S. application Ser. No. 14/457,850, filed on Aug. 12, 2014; which claims priority to U.S. Provisional Application Ser. No. 61/866,347, filed Aug. 15, 2013, the entire content of each being hereby expressly incorporated herein by reference.

BACKGROUND

The distal tibiofibular syndesmosis is usually described as being comprised of four ligaments. These ligaments are the anterior inferior tibiofibular ligament (AITFL), the posterior inferior tibiofibular ligament (PITFL), the transverse ligament (TL), and the interosseous ligament (IL). The primary role of these ligaments is to act as tensile members that stabilize the fibula within the distal tibiofibular joint. Injury to these ligaments, either isolated or concomitant with fractures of one or both the tibia and fibula, results in diastasis of the ankle joint which manifests as ankle instability.

Due to diagnostic and surgical limitations, direct repair of the ligaments is normally not performed, except in the case of the AITFL which is easily appreciated during the normal surgical dissection used to place a fracture plate on the fibula. Stabilization is the more common surgical intervention method, and several implants have been developed through the years.

The most common implant used to stabilize the distal tibiofibular joint is the cortical screw. One or two screws ranging in diameter from 3.5 mm to 4.5 mm are typically used. The screws are placed through the fibula, most often engaging both cortices, and then placed into the tibia either engaging one or two of the cortices. While the screws provide excellent stabilization, they cannot withstand the increasing displacement demands of the healing joint. This results in the screws commonly failing or restricting motion of the joint; leading to the need to perform a second surgery for hardware removal.

Many of the other implants developed for treating this pathology utilize the rigid method employed by the screw to stabilize the joint. However, a more recent entry on the market utilizes a flexible member to provide stability without the rigidity. This implant, known as the TightRope® from Arthrex®, utilizes two buttons connected by a flexible central member made from suture. One button is placed on the medial cortex of the tibia and the other button is placed on the lateral cortex of the fibula (or on top of a fracture plate on the fibula). The suture member runs through the tibia and fibula connecting the two plates. This transition from rigid to flexible seems to maintain enough stability not to influence clinical outcomes and reduces the incidences of broken hardware and stiff joints.

While an apparent improvement upon the rigid implants, the TightRope® implant is not without its shortcomings. Due to its fixation members being placed on the bones, there have been reports of tissue irritation. Also, in some cases a single TightRope® implant does not offer enough stability, and it is recommended that two be used. This could be due to strength concerns, but also due to the single point of fixation the construct offers. While like a ligament in that it is a tensile stability member, it is unlike them in that it is a singular member trying to replace multiple members. As tensile members only function in tension, more than one is needed if multiple degrees of freedom need to be controlled.

With flexible, and even modified rigid constructs, providing a possible avenue to reduce certain post-operative complications, attention to the reduction of the distal tibiofibular joint has increased due to its seemingly greater influence on clinical outcomes regardless of the stabilization method employed. Neither screws nor the TightRope® implant directly address this need. Reduction is currently carried out as a separate preceding step to implant delivery, and the implants reinforce good reductions, as well as poor. Cortical screws offer no correction. The TightRope® implant, as communicated by surgeons, does allow for some self-correction due to its flexibility, but this ability has limitations.

SUMMARY OF THE INVENTIVE CONCEPTS

The inventive concepts disclosed herein attempt to address the shortcomings of the devices briefly described above. More specifically, the inventive concepts attempt to incorporate the positive attributes of the flexible stabilization implants, such as reducing the need for removal surgery due to implant breakage and joint stiffness, while improving upon the profile and stability, while also introducing the ability to facilitate reduction during implant delivery.

The inventive concepts disclosed herein accomplish this through the use of one or more anchors in the lateral aspect of the tibia that connect via self-locking, adjustable suture loops that extend around the fibula to the lateral aspect of the fibula. The inventive concepts disclosed herein can simulate native ligaments and thus be used to re-establish the boundaries of the tibiofibular joint and be used to guide the reduction of the tibiofibular joint. The inventive concepts can also provide multiple tension stabilization vectors to provide adjustable stabilization of the tibiofibular joint.

BRIEF DESCRIPTION OF THE DRAWINGS

To assist those of ordinary skill in the relevant art in making and using the inventive concepts disclosed herein, reference is made to the appended drawings and schematics, which are not intended to be drawn to scale, and in which like reference numerals may refer to the same or similar elements for consistency. For purposes of clarity, not every component may be labeled in every drawing. Certain features and certain views of the figures may be shown exaggerated in scale or in schematic in the interest of clarity and conciseness. In the drawings.

DETAILED DESCRIPTION OF EXEMPLARY EMBODIMENTS

Figure 1A:
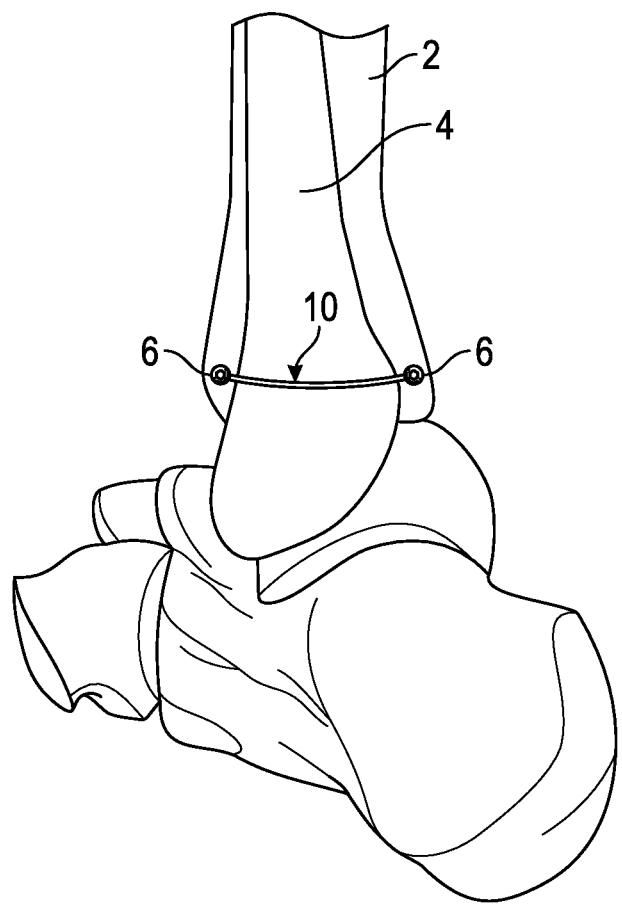
FIG. 1A is an oblique view of a schematic illustration of a fibula band assembly constructed in accordance with the inventive concepts disclosed herein.

Before explaining at least one embodiment of the presently disclosed and claimed inventive concepts in detail, it is to be understood that the presently disclosed and claimed inventive concepts are not limited in their application to the details of construction, experiments, exemplary data, and/or the arrangement of the components set forth in the following description or illustrated in the drawings. The presently disclosed and claimed inventive concepts are capable of other embodiments or of being practiced or carried out in various ways. Also, it is to be understood that the phraseology and terminology employed herein is for purpose of description and should not be regarded as limiting.

In the following detailed description of embodiments of the inventive concepts, numerous specific details are set forth in order to provide a more thorough understanding of the inventive concepts. However, it will be apparent to one of ordinary skill in the art that the inventive concepts within the disclosure may be practiced without these specific details. In other instances, certain well-known features may not be described in detail to avoid unnecessarily complicating the instant disclosure.

As used herein, the terms "comprises," "comprising," "includes," "including," "has," "having," or any other variation thereof, are intended to cover a non-exclusive inclusion. For example, a process, method, article, or apparatus that comprises a list of elements is not necessarily limited to only those elements but may include other elements not expressly listed or inherently present therein.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present).

The term "and combinations thereof" as used herein refers to all permutations or combinations of the listed items preceding the term. For example, "A, B, C, and combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. A person of ordinary skill in the art will understand that typically there is no limit on the number of items or terms in any combination, unless otherwise apparent from the context.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

The use of the terms "at least one" and "one or more" will be understood to include one as well as any quantity more than one, including but not limited to each of, 2, 3, 4, 5, 10, 15, 20, 30, 40, 50, 100, and all integers and fractions, if applicable, therebetween. The terms "at least one" and "one or more" may extend up to 100 or 1000 or more, depending on the term to which it is attached; in addition, the quantities of 100/1000 are not to be considered limiting, as higher limits may also produce satisfactory results.

Further, as used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein qualifiers such as "about," "approximately," and "substantially" are intended to signify that the item being qualified is not limited to the exact value specified, but includes some slight variations or deviations therefrom, caused by measuring error, manufacturing tolerances, stress exerted on various parts, wear and tear, and combinations thereof, for example.

As used herein, the term "patient" is meant to include all organisms, whether alive or dead, including any species having soft tissues and bones. For example, a method according to the inventive concepts disclosed herein may be used to repair a soft tissue detachment injury in a living human, horse, cow, sheep, cat, dog, and the like. In another example, a method according to the inventive concepts disclosed herein may be used in a non-living organism to train medical personnel in surgical techniques. As yet another example, a method according to the instant disclosure may be used to implant medical devices such as replacement joints, pacemakers, and the like, into an organism by anchoring such devices to a bone. As yet another example, a method according to the inventive concepts disclosed herein may be used to repair rotator cuff instabilities and tears in shoulder surgery, or to repair various knee, elbow, hip, wrist, ankle, or other soft tissue detachment and joint injuries.

Figure 1B:
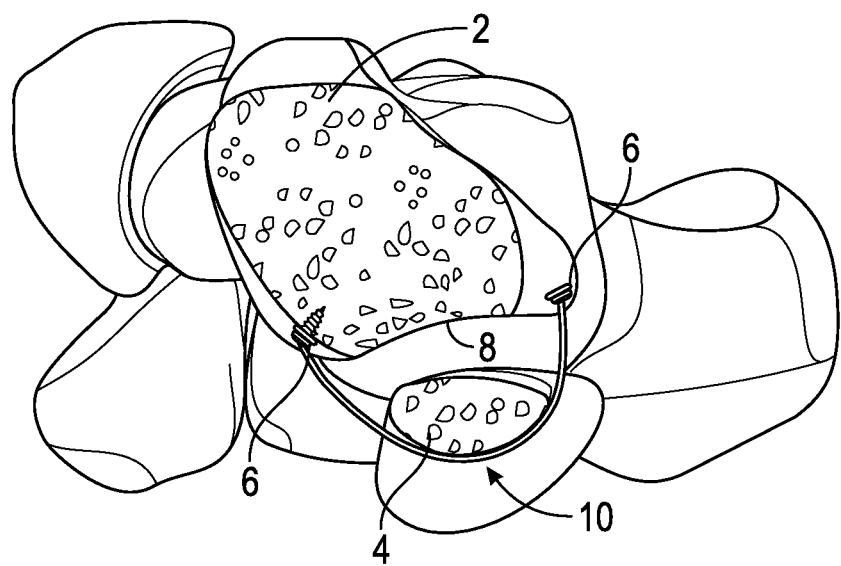
FIG. 1B is an axial view of a schematic illustration of a fibula band assembly constructed in accordance with the inventive concepts disclosed herein.

Referring now to the drawings, and more particularly to FIGS. 1A and 1B, a fibula band assembly 10 is schematically shown connected to the tibia 2 and positioned around the fibula 4 to secure the fibula 4 into place within the fibula notch 8 of the tibia 2. Because the original physiology and ligaments were based on the sides and around the tubercles 6 of the tibia 2, the apparatus and procedures disclosed herein focuses on using anchors in the lateral aspects of the tibia 2 as fixation points. For example, by using the tubercles 6, or the area near the tubercles 6, as fixation points, the fibula band assembly 10 can be placed around the fibula 4 at substantially the same level as the fibular notch 8. As such, the fibula band assembly 10 can mimic native ligaments so as to restrict lateral motion of the fibula while also reducing the fibula to the tibia.

Figure 2A:
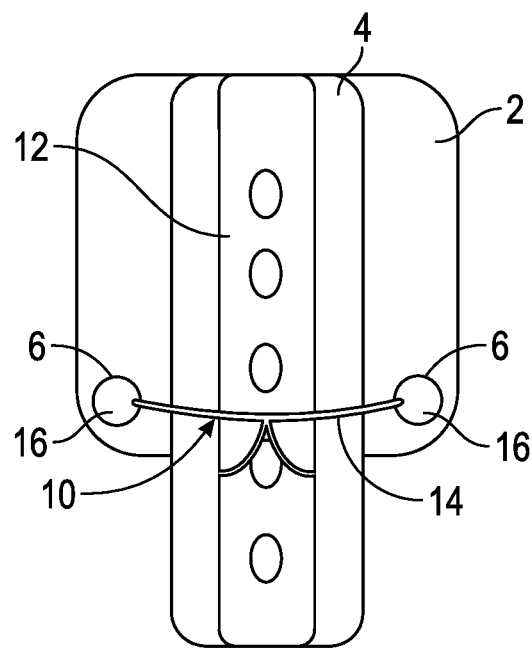
FIG. 2A is a diagrammatic, elevation view of a fibula band assembly shown positioned in a bone.
Figure 2B:
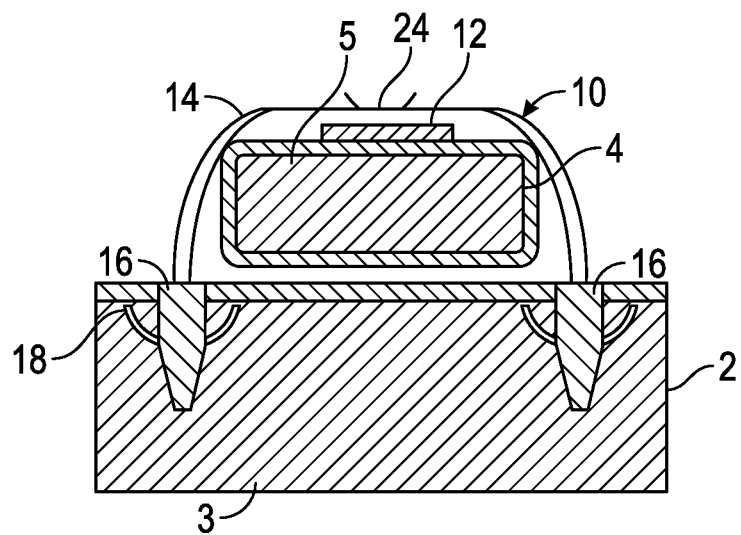
FIG. 2B is a diagrammatic, cross sectional view of the fibula band assembly of FIG. 2A.
Figure 2C:
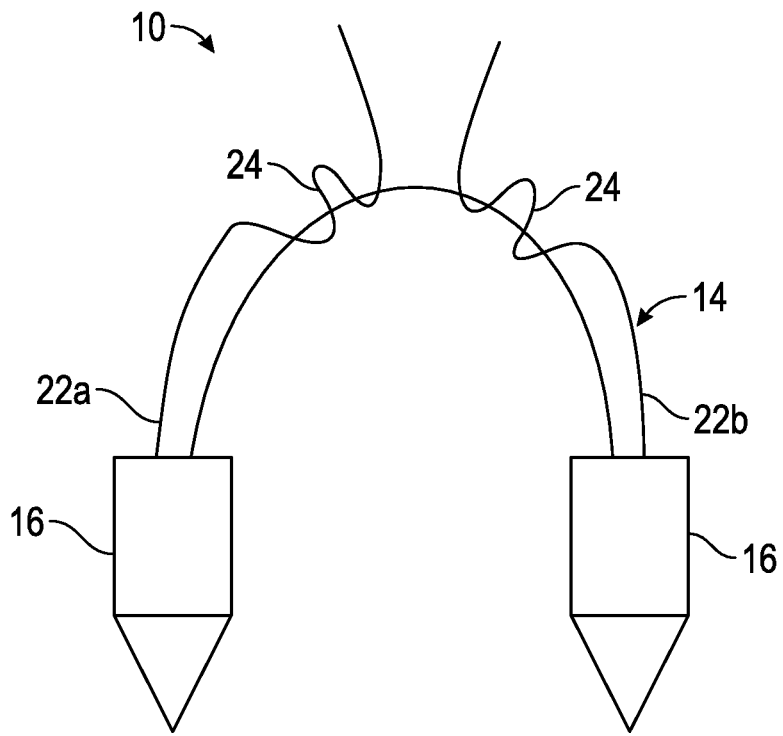
FIG. 2C is a schematic illustration of the fibula band assembly of FIG. 2A.

Referring now to FIGS. 2A-2C, one embodiment of a fibula band assembly 10 is diagrammatically shown positioned around the fibula 4 and secured to the tibia 2. The fibula band assembly 10 includes at least two suture anchors 16 and a suture assembly 14. The suture anchors 16 are adapted to be positioned in or near the tubercles 6 of the tibia 2 on opposing sides of the fibular notch 8 (FIG. 1A).

Figure 3A:
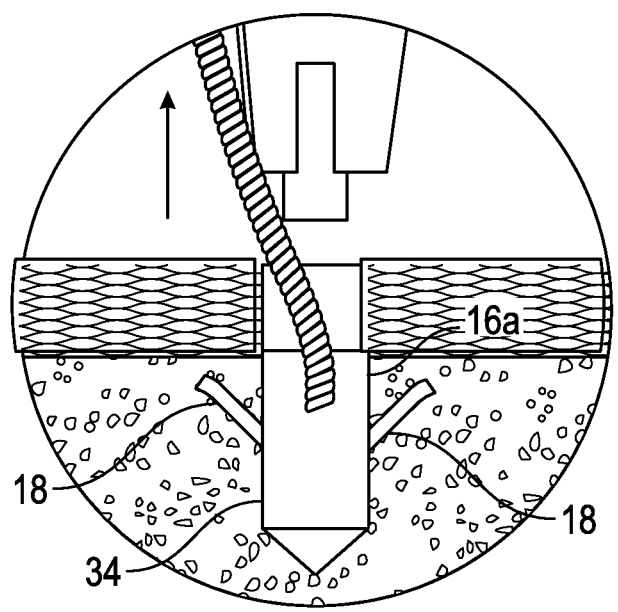
FIG. 3A is a schematic illustration of one embodiment of a suture anchor.

As best illustrated in FIG. 3A, the suture anchors 16 may have a body 34 configured to be inserted into the tibia 2. The body 34 has a proximal end, a distal end, and a sidewall extending between the proximal end and the distal end. The sidewall may be provided with at least one bone engaging member 18, illustrated as prongs, which prevent the suture anchor 16 from being dislodged from the internal bone of the tibia 2. Thus, the fibula band assembly 10 is attached and secured to the fibula 4 without needing to attach an apparatus into the internal bone 5 (FIG. 2B) of the fibula 4.

Figure 3B:
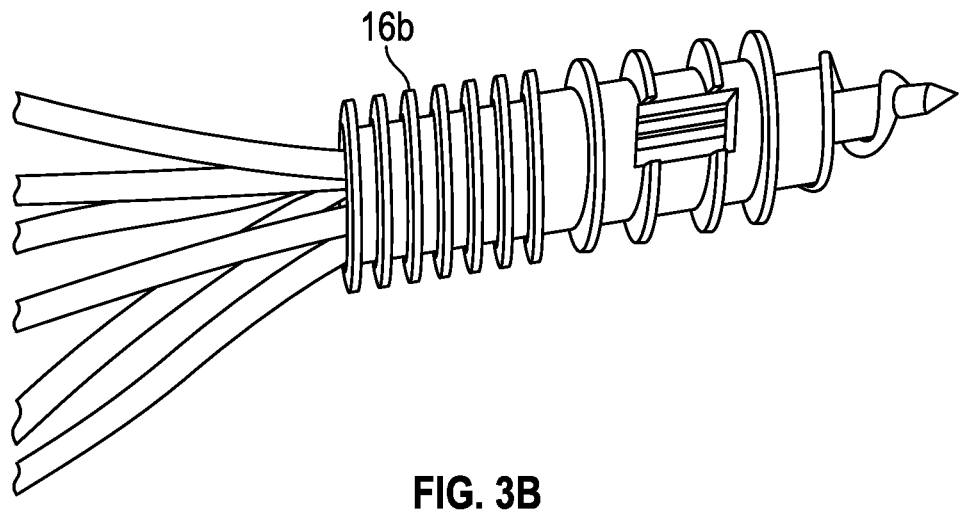
FIG. 3B is a perspective view of another embodiment of a suture anchor.
Figure 3C:
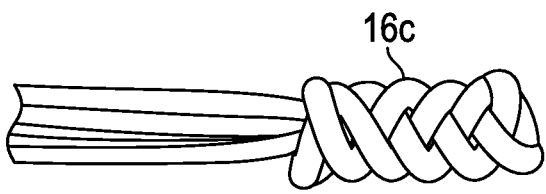
FIG. 3C is an elevational view of another embodiment of a suture anchor.
Figure 3C:
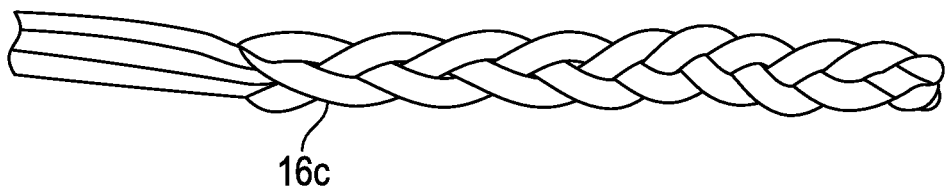

It should be appreciated that the suture anchors 16 may be any suitable suture anchor. By way of example, the suture anchors 16 may be one of generally three types. First, the suture anchors 16 may be a push-in style anchor 16a (e.g., Mitek G2 anchor). This type of anchor offers easy, axial insertion, but removal is difficult. An example is shown in FIG. 3A. Second, the suture anchors may be a screw style anchor 16b (e.g., Mitek Healix). This type of anchor offers a combination of pull-out strength, ease-of-use, and simplicity. An example is shown in FIG. 3B. Third, as illustrated in FIG. 3C, the suture anchors may be an expanding style anchor 16c (e.g., knot anchor). This type of anchor offers an all-suture construction and the ability to adjust to bone quality, but complexity is higher than the others.

The various anchors disclosed serve to provide an anchor point for the suture assembly 14. Therefore, it should also be appreciated that the suture anchors 16 may include a variety of features and mechanisms used to secure the body of the suture anchor 16 to the bone. By way of example but not limitation, the features and mechanisms may include barbs, ribs, teeth and/or other anchor-securing mechanisms of the sort well known in the art. In addition to the foregoing, other approaches can be used to secure the body of the anchor in the bone, e.g., the body can be hammered into the bone like a nail, or the anchor can be toggled upon entry into the bone so as to prevent its withdrawal.

Although examples of suture anchors that may be employed with the suture anchor assemblies are disclosed herein. Other examples of suture anchors, which employ suture capture elements, are disclosed in U.S. Publication. Nos. 2009/0088798 and 2012/0150223, as well as U.S. patent application Ser. No. 13/430,201 and 61/683,382, each of which are hereby expressly incorporated herein by reference.

As illustrated in FIG. 2C, the suture assembly 14 may include a pair of loops 22a and 22b formed on opposing ends of the suture assembly 14. The loops 22a and 22b are adapted to be captured by a suture capture element of the suture anchor 16 either before or after the suture anchor 16 has been deployed in bone. The suture assembly 14 further may further include one or more regions 24 whereby a first strand segment is woven into or threaded through a second strand segment to define a section that permits the tension of the suture assembly 14 to be adjusted with or without the tying of a knot. By way of example, the sutures may be formed as disclosed in U.S. Publication. No. 2012/0150223, which is hereby expressly incorporated herein by reference.

In other embodiments of the suture assembly, the strand segments may be separate segments, each provided with a static loop. Also, any number of pre-tied, sliding knots commonly employed in arthroscopic surgery (e.g., a Giant knot, an SMC knot, a Weston knot) may be incorporated into the suture assembly to provide a "knotless" connection structure. Also, a hard fastener, such as a clamp or crimp, may be employed to lock the strands.

Figure 4A:
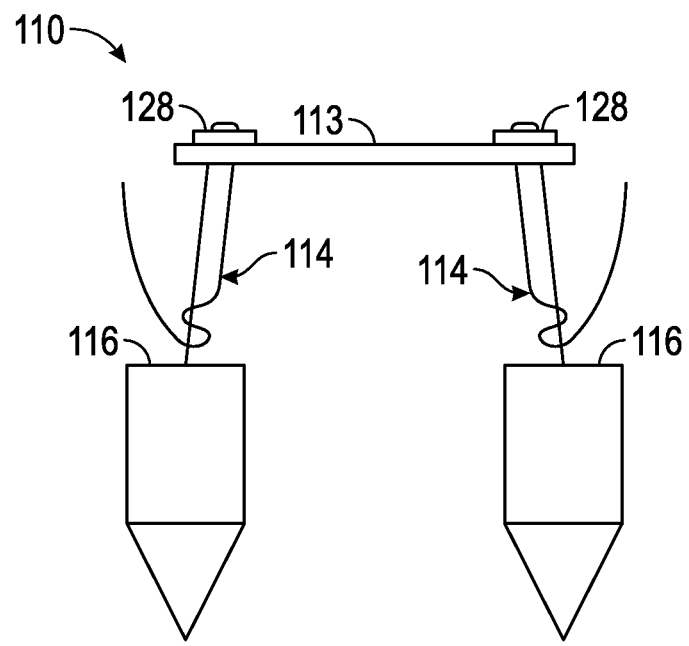
FIG. 4A is a schematic illustration of another embodiment of a fibula band assembly.
Figure 4B:
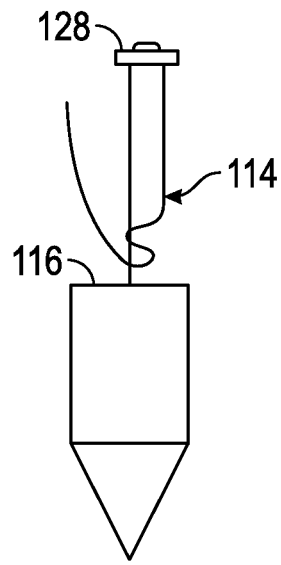
FIG. 4B is a schematic illustration of a suture anchor and suture assembly combination for use in the fibula band assembly of FIG. 4A.
Figure 4C:
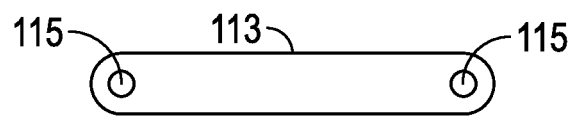
FIG. 4C is a top plan view of a suture coupling.

FIGS. 4A-4C illustrate another embodiment of a fibula band assembly 110 featuring a suture coupling 113. The fibula band assembly 110 broadly includes a plurality of anchors 116 and a plurality of suture assemblies 114. The suture assemblies 114 may include any suitable suture assembly, similar to those described above. More specifically, each of the suture loop assemblies 114 has one end looped or otherwise secured to the suture anchor 116 and another end looped through or around a suture fixation member, such as a toggle anchor 128. As such, the suture assembly 114 is adapted to be integrated with the suture coupling 113, as shown in FIG. 4A. Each toggle anchor 128 is threaded through an aperture 115 (FIG. 4C) of the suture coupling 113, and the suture assembly 114 is then cinched or otherwise pulled to the desired tension. Thereafter, the non-tensioned extra suture material adjacent to the toggle anchor 128 is trimmed away.

The suture anchors 116 may be any suitable suture anchors, such as described above in connection with the suture anchors 16.

In one embodiment, the suture coupling 113 may be a thin, flat body which may be fabricated of a relatively soft or pliable bio-inert material, such as a textile material (e.g., any cloth, or goods produced by weaving, knitting, braiding, twisting, or felting, of one or more fibers or other materials), a foam material, polyethylene, polyurethane, PLA, PLGA, Ultra High Molecular Weight Polyethylene fibers, and combinations thereof, for example. A soft or pliable material would allow the suture coupling 113 to conform to the contour of the surface of the bone or a plate, and to have no sharp edges, thereby minimizing soft tissue irritation. Further, the suture coupling 113 may be folded and inserted though the cannula of an arthroscopic surgical instrument, for example. The suture coupling 113 may be used to attach one or more sutures assemblies, such as by tying or looping one or more suture assemblies 114 to the suture coupling 113, or by sewing one or more suture assemblies 114 into the suture coupling 113, or combinations thereof, for example. The suture coupling 113 may be coated or impregnated with a variety of substances, including but not limited to antibiotics, healing agents, anti-clotting agents, anti-inflammatory agents, or combinations thereof, for example. The suture coupling 113 may have its edges and suture apertures reinforced, such as by braiding or weaving a second layer of material interlinked with the coupling base during the manufacture of the suture coupling 113, for example. The suture coupling 113 may formed in a variety of shapes. For example, as shown in FIG. 4C, the suture coupling 113 is generally in the shape of a strip having a slit or hole 115 near each end thereof.

Figure 5A:
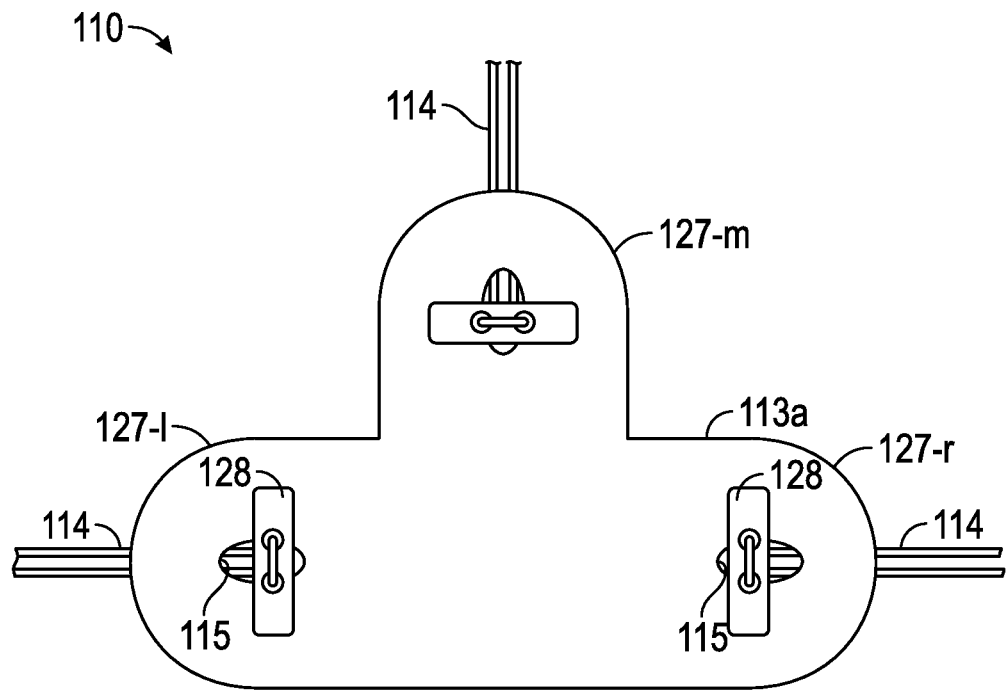
FIG. 5A is top plan view of another embodiment of suture coupling.

In FIG. 5A, a suture coupling 113a is shown as being configured to have a plurality of appendages 127. Each appendage 127 may include an aperture 115 for receiving the suture assembly 114 and the toggle anchor 128. The suture coupling 113 illustrated in FIG. 5A includes a third appendage 127-*m* that is medial to the left and right 127-*l*, 127-*r* appendages. The medial appendage 127-*m* may be used to either secure the suture coupling 113 to the fibula alone, or based on its medial positioning may be used to anchor another suture assembly 114 into the tibia 2 while passing though the fibula 4, and serving as a through band to create a lateral support. Thus, the fibula band assembly 110 includes the possibility of at least three tibia fixation points. The medial point however requires drilling through the fibula 4 to access the tibia 2 which may not always be an option if a patient's fibula is fractured. Thus, the medial appendage 127-*m* may be considered an optional appendage at time of use and thus may remain unsecured, secured into the fibula only, or trimmed away. As will be discussed below, some suture couplings may include screw apertures for screw fixation. However, the suture coupling 113 shown does not employ screw fixation and may be held in place merely by the tension of the suture assemblies 114. Optionally, and not shown, the suture coupling 113 may be indirectly fixed by being sandwiched between the fibula 4 and a bone plate 12 (FIGS. 2A and 2B) by being tensioned and placed directly onto the fibula 4 before a bone plate 12 is added.

Figure 5B:
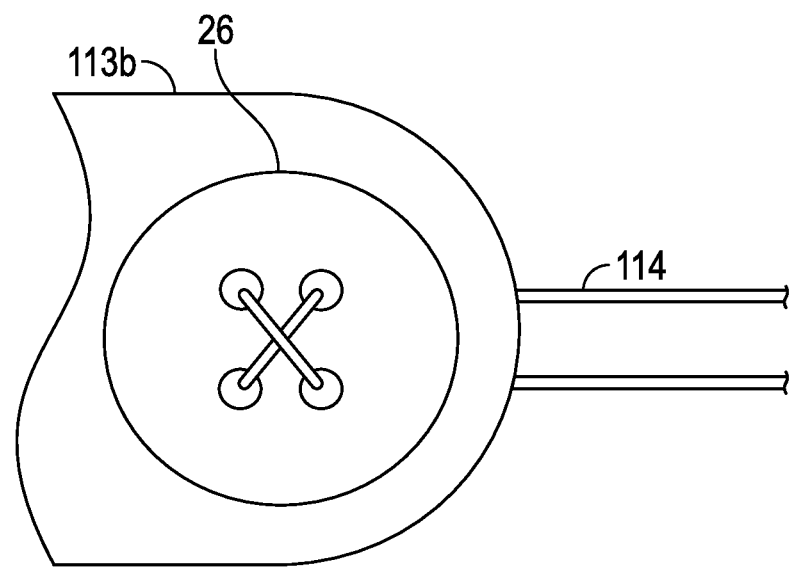
FIG. 5B is a plan view of another exemplary embodiment of a suture coupling.

FIG. 5B illustrates a suture coupling 113b provided with one or more buttons 26 attached to the suture coupling 113b such that a loop of a suture assembly 114 may be looped around the button 26 to secure the suture assembly 114 to the suture coupling 113b.

Referring to FIGS. 6-28, various embodiments of fibula band assemblies featuring various suture couplings are illustrated. Generally, the suture couplings may include a central body that contacts the fibula on its lateral side and includes suture fixation points for suture loops to attach. The suture coupling may be made from various materials (e.g., metal, polymers, textile materials, and combinations thereof).

Figure 6A:
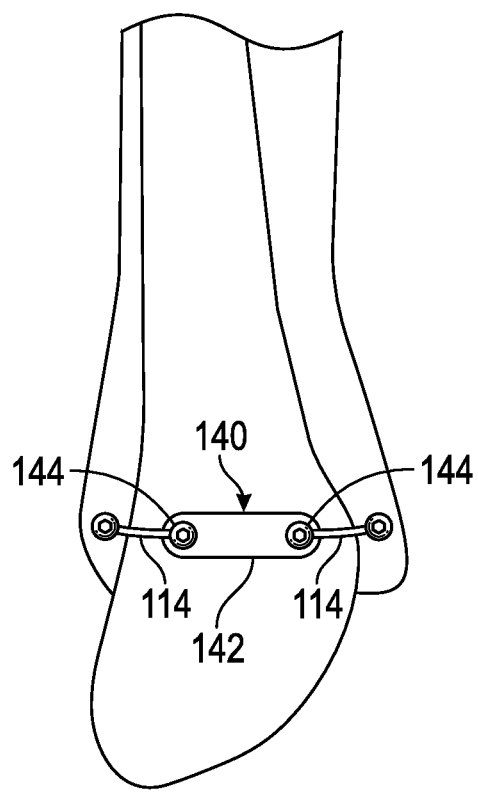
FIG. 6A is a lateral view of a portion of a tibia and fibula showing another embodiment of a fibula band assembly positioned to stabilize and reduce the fibula relative to the tibia.
Figure 6B:
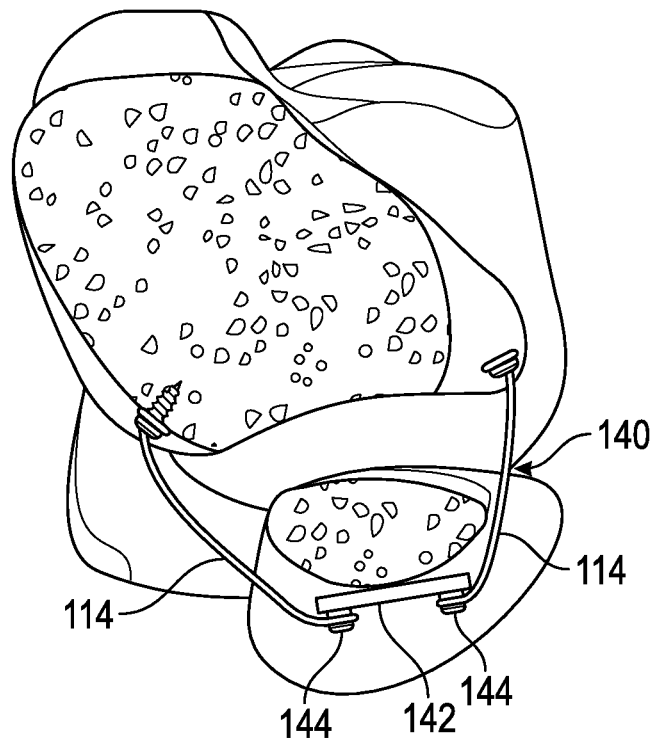
FIG. 6B is an axial view of the fibula band assembly of FIG. 6A.
Figure 7A:
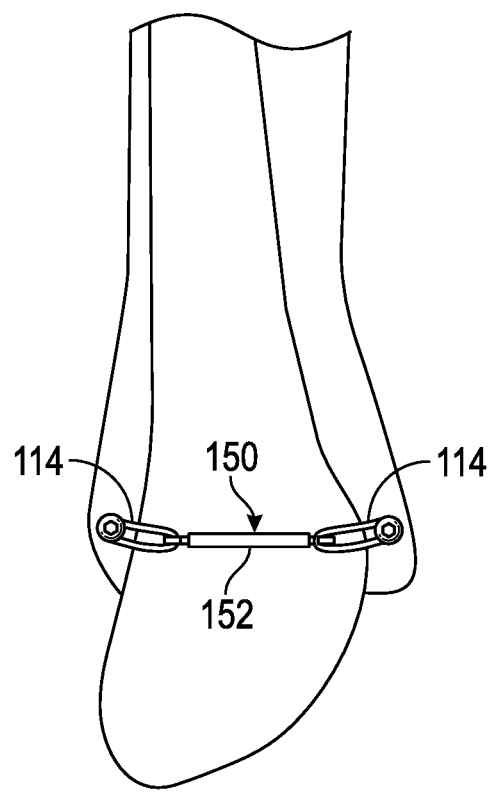
FIG. 7A is a lateral view of a portion of a tibia and fibula showing another embodiment of a fibula band assembly positioned to stabilize and reduce the fibula relative to the tibia.
Figure 7B:
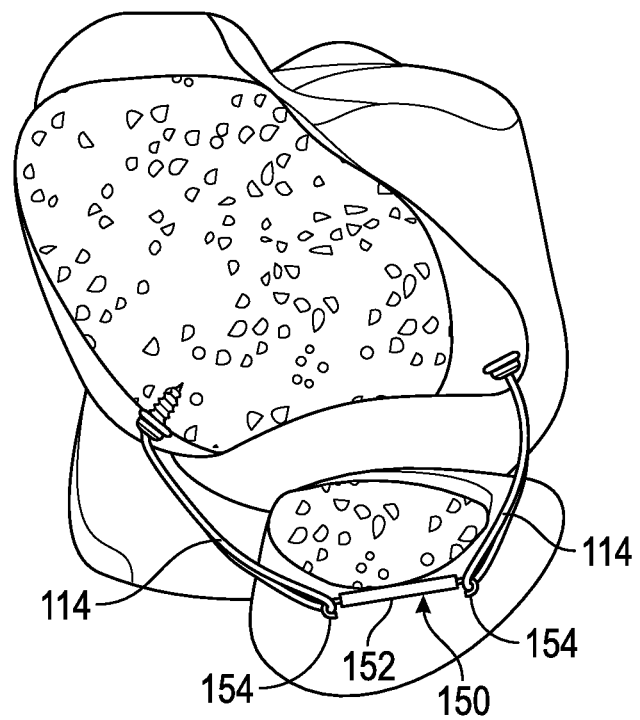
FIG. 7B is an axial view of the fibula band assembly of FIG. 7A.
Figure 8A:
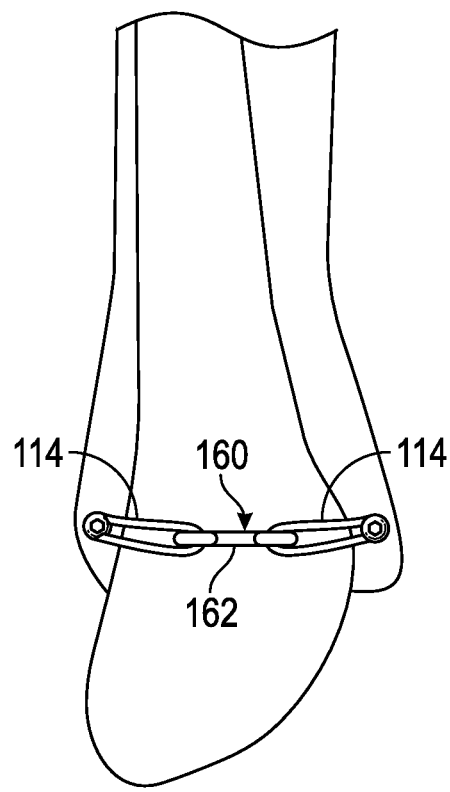
FIG. 8A is a lateral view of a portion of a tibia and fibula showing another embodiment of a fibula band assembly positioned to stabilize and reduce the fibula relative to the tibia.
Figure 8B:
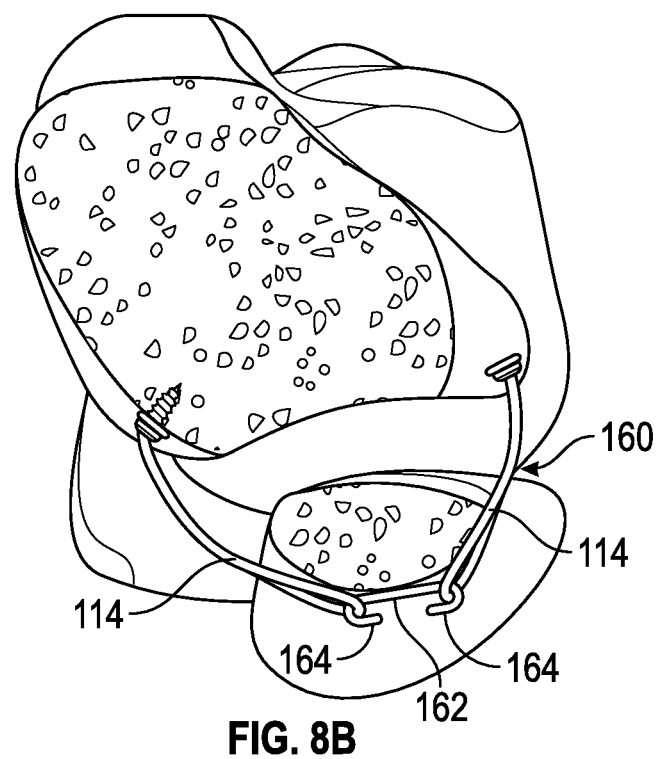
FIG. 8B is an axial view of the fibula band assembly of FIG. 8A.
Figure 9A:
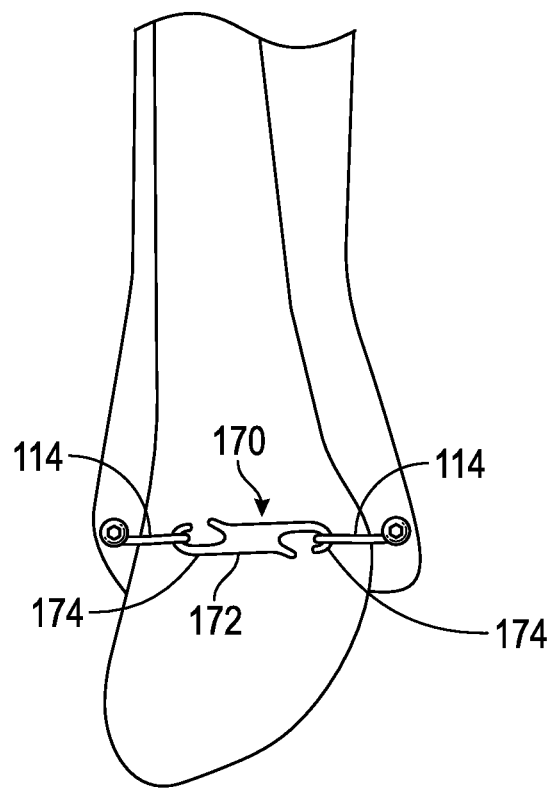
FIG. 9A is a lateral view of a portion of a tibia and fibula showing another embodiment of a fibula band assembly positioned to stabilize and reduce the fibula relative to the tibia.
Figure 9B:
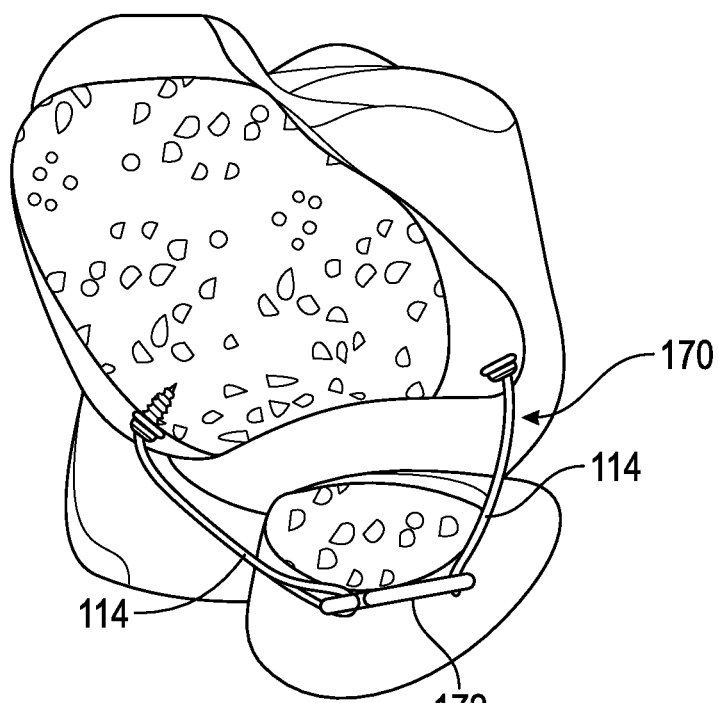
FIG. 9B is an axial view of the fibula band assembly of FIG. 9A.
Figure 10:
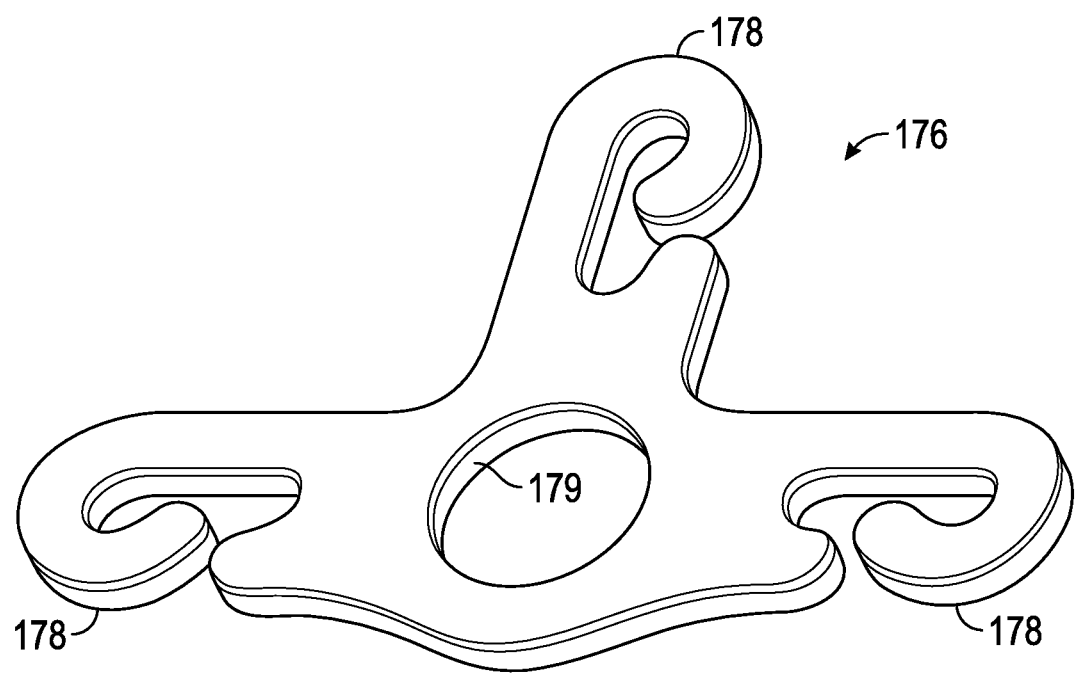
FIG. 10 is a perspective view of another embodiment of a suture coupling.

FIGS. 6A and 6B illustrate a fibula band assembly 140 that includes a suture coupling 142 with a plurality of spools 144 for receiving the loops of a pair of suture assemblies 114. FIGS. 7A and 7B illustrate a fibula band assembly 150 that includes a suture coupling 152 with a plurality of hooks 154 on opposing ends of the suture coupling 152 for receiving the loops of a pair of suture assemblies 114. FIGS. 8A and 8B illustrate a fibula band assembly 160 that includes another embodiment of a suture coupling 162 with a plurality of hooks 164 on opposing ends of the suture coupling 162 for receiving the loops of a pair of suture assemblies 114. FIGS. 9A and 9B illustrate a fibula band assembly 170 that includes a suture coupling 172 with a plurality of clips 174 for receiving the loops of a pair of suture assemblies 114. FIG. 10 illustrates a suture coupling 176 with three clips 178 for receiving the loops of three suture assemblies 114 and a hole 179 for receiving a connector, such as a screw in a manner to be discussed below.

Figure 11:
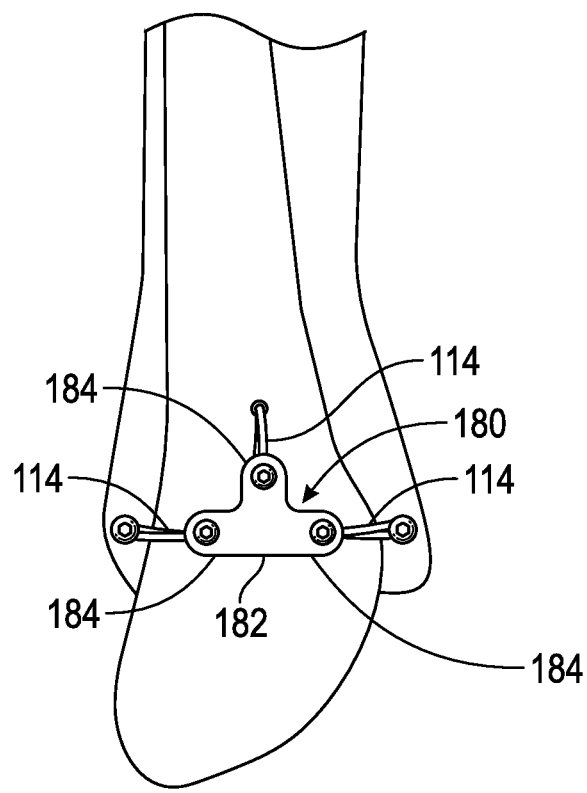
FIG. 11 is a lateral view of a portion of a tibia and fibula showing another embodiment of a fibula band assembly positioned to stabilize and reduce the fibula relative to the tibia.
Figure 12:
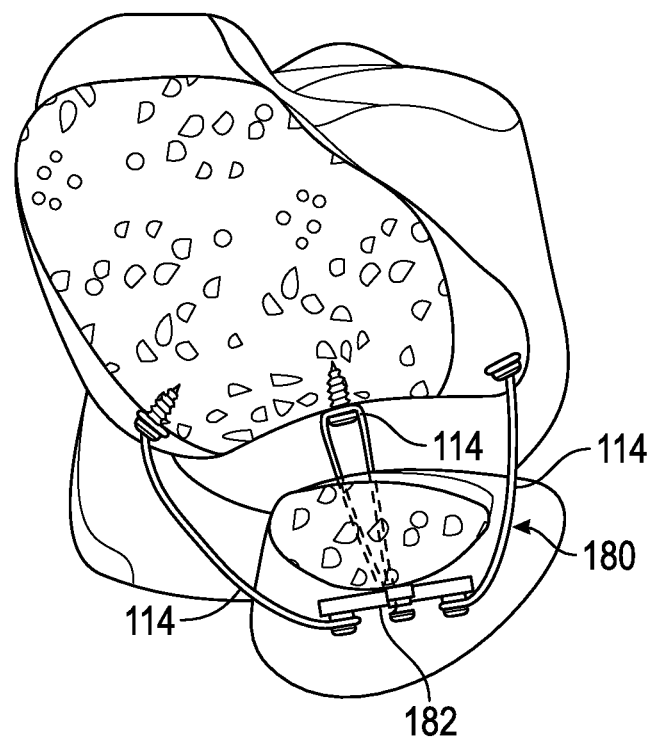
FIG. 12 is an axial view of the fibula band assembly of FIG. 11.
Figure 13A:
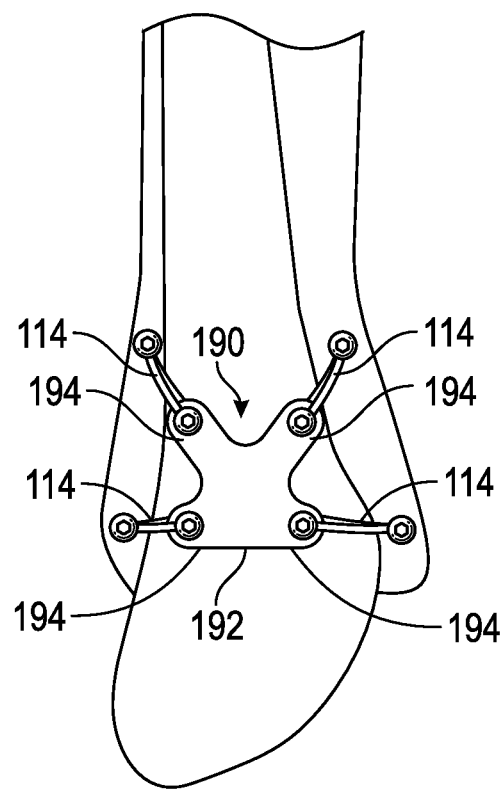
FIG. 13A is a lateral view of a portion of a tibia and fibula showing another embodiment of a fibula band assembly positioned to stabilize and reduce the fibula relative to the tibia.
Figure 13B:
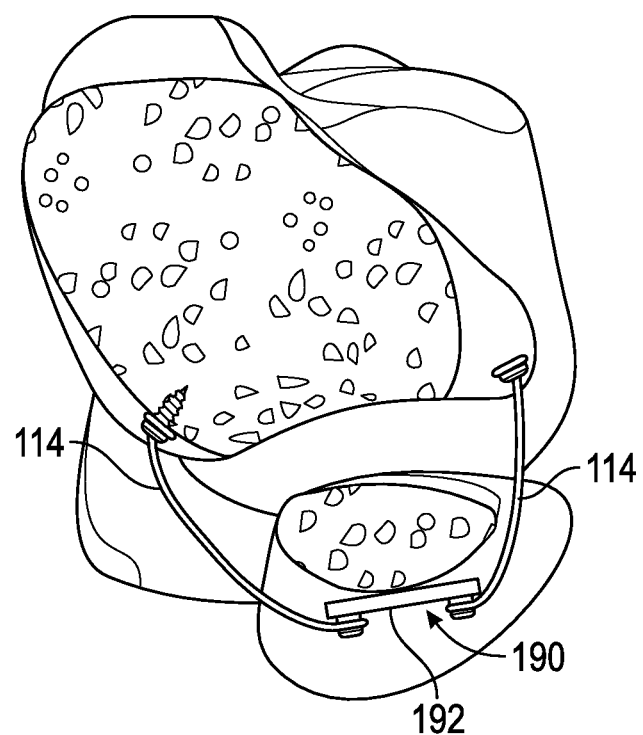
FIG. 13B is an axial view of the fibula band assembly of FIG. 13A.
Figure 14A:
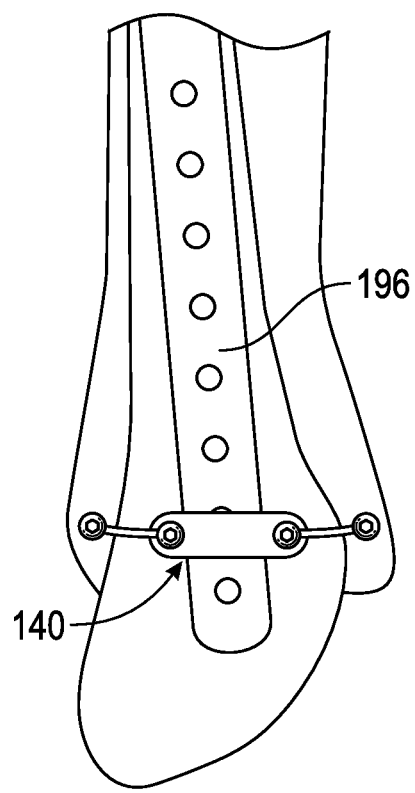
FIG. 14A is a lateral view of a portion of a tibia and fibula showing another embodiment of a fibula band assembly positioned to stabilize and reduce the fibula relative to the tibia.
Figure 14B:
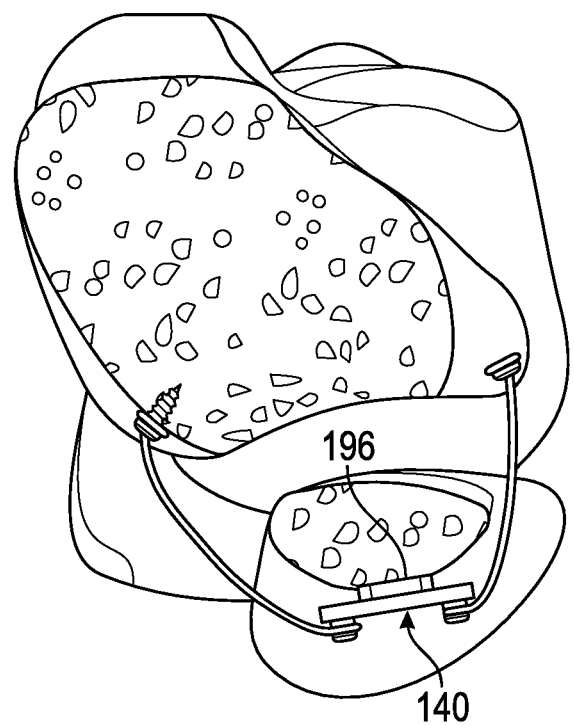
FIG. 14B is an axial view of the fibula band assembly of FIG. 14A.
Figure 15A:
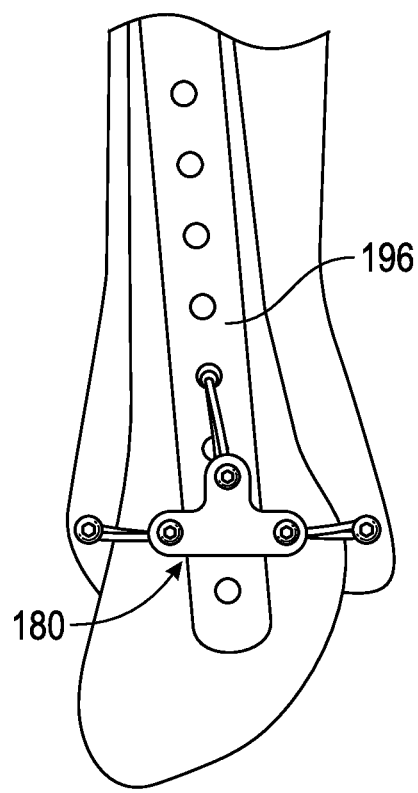
FIG. 15A is a lateral view of a portion of a tibia and fibula showing another embodiment of a fibula band assembly positioned to stabilize and reduce the fibula relative to the tibia.
Figure 15B:
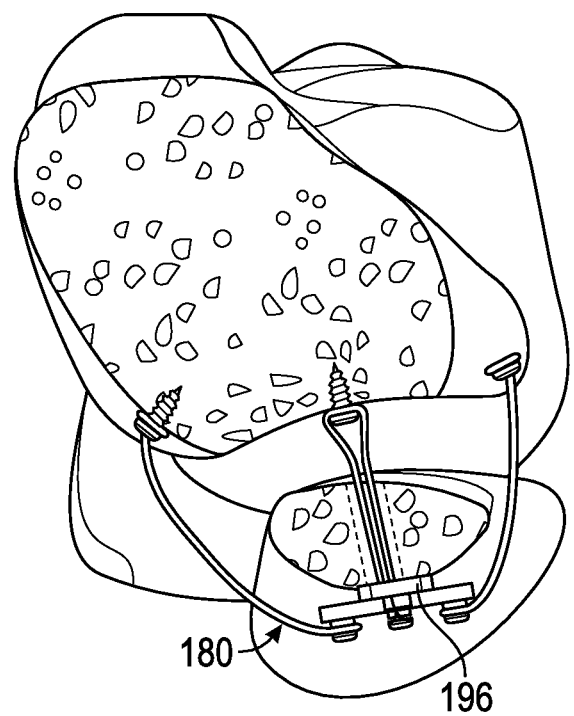
FIG. 15B is an axial view of the fibula band assembly of FIG. 15A.
Figure 16A:
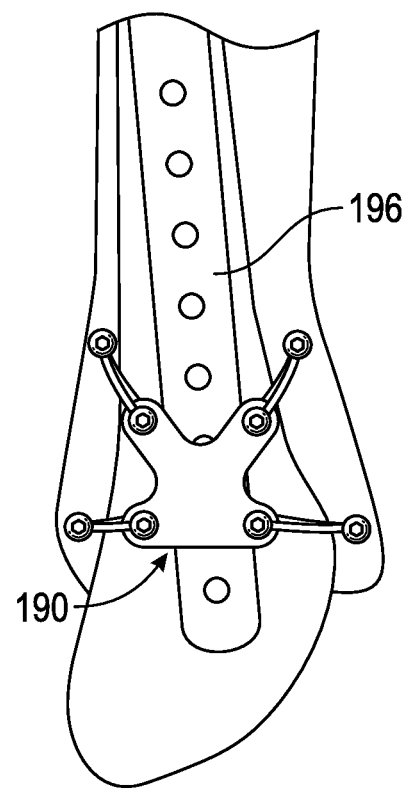
FIG. 16A is a lateral view of a portion of a tibia and fibula showing another embodiment of a fibula band assembly positioned to stabilize and reduce the fibula relative to the tibia.
Figure 16B:
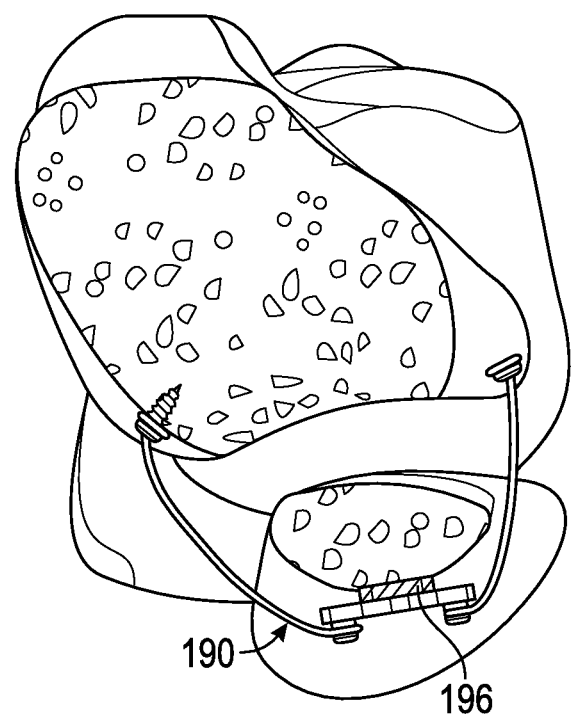
FIG. 16B is an axial view of the fibula band assembly of FIG. 16A.

FIGS. 11 and 12 illustrate a fibula band assembly 180 that includes a suture coupling 182 with three appendages 184 for receiving the loops of three suture assemblies 114. FIGS. 13A and 13B illustrate a fibula band assembly 190 that includes a suture coupling 192 with four appendages 194 for receiving the loops of four suture assemblies 114. FIGS. 14A-16B illustrate the fibula band assemblies 140, 180, and 190, respectively, in combination with a fracture plate 196.

Figure 17A:
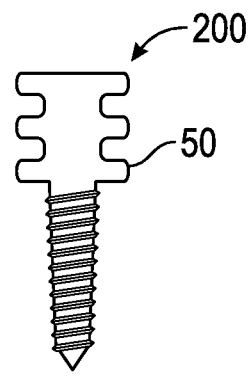
FIG. 17A is an elevational view of another embodiment of a suture coupling.
Figure 17B:
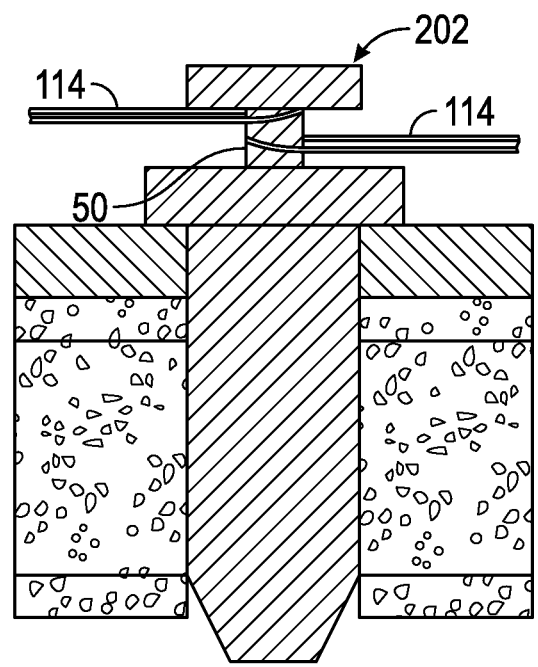
FIG. 17B is diagrammatic, sectional view of another embodiment of a suture coupling.

FIGS. 17A and 17B illustrate suture couplings 200 and 202, respectively, in the form of a screw that may be dimensioned to extend through a bone plate on the fibula 4 and into the internal bone 5 of the fibula 4. A head of the screw may include one or more circumferential grooves 50 to accept suture loops. In another version, the screw may have a capture element, such as disclosed in U.S. Pat. No. 8,388,654 issued to Snyder et al., which is hereby expressly incorporated herein by reference.

Figure 18:
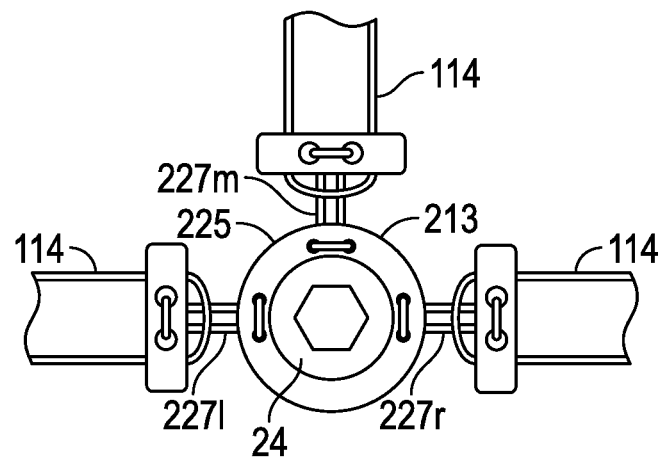
FIG. 18 is a plan view of another embodiment of a suture coupling.

With reference to FIG. 18, another embodiment of a suture coupling 213 is illustrated. The suture coupling 213 is made of a relatively flexible body 225 and has three appendages 227 including appendage 227-*m* that is medial to the other two left and right 227-*l*, 227-*r* appendages. The medial appendage 227-*m* is optionally used to either help secure the suture coupling 213 to the fibula alone, or based on its medial positioning may be used to anchor a suture assembly 114 into the tibia 2 while passing though the fibula 4 to create a lateral support similar to the above discussed tightrope approach. The suture coupling 213 includes a screw aperture (not visible) for screw fixation of the suture coupling 213 onto the fibula 4 by placing a screw 24 into the suture coupling screw aperture. The screw 24 may be sized such that it is just long enough to secure the suture coupling 213 onto the fibula 4 wherein the screw threads reside within the internal bone 5 of the fibula 4. Additional embodiments contemplated having a tibia/fibula screw having a length such that the screw extends through the fibula and into at least a portion of the tibia will be discussed below.

Figure 19A:
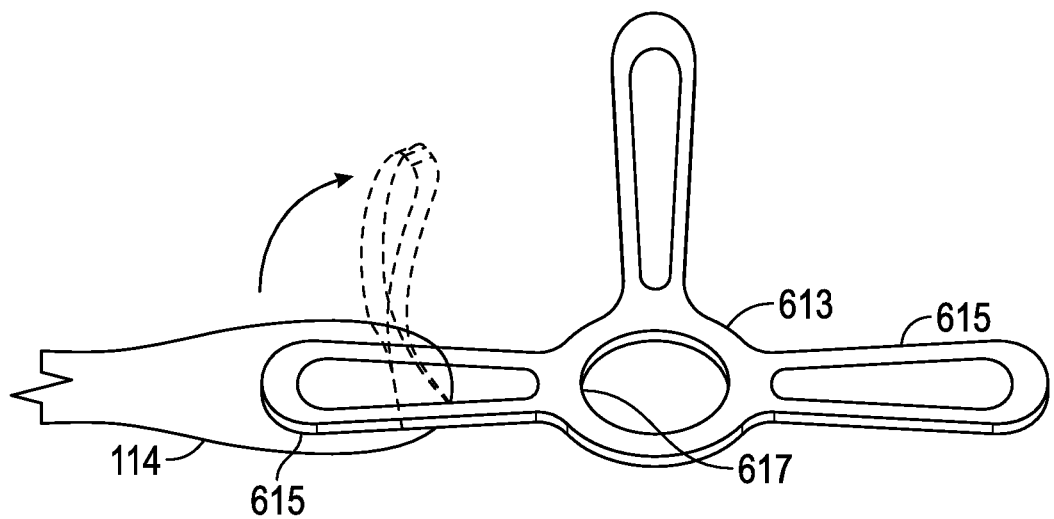
FIG. 19A is a perspective view of another embodiment of a suture coupling in an open position.
Figure 19B:
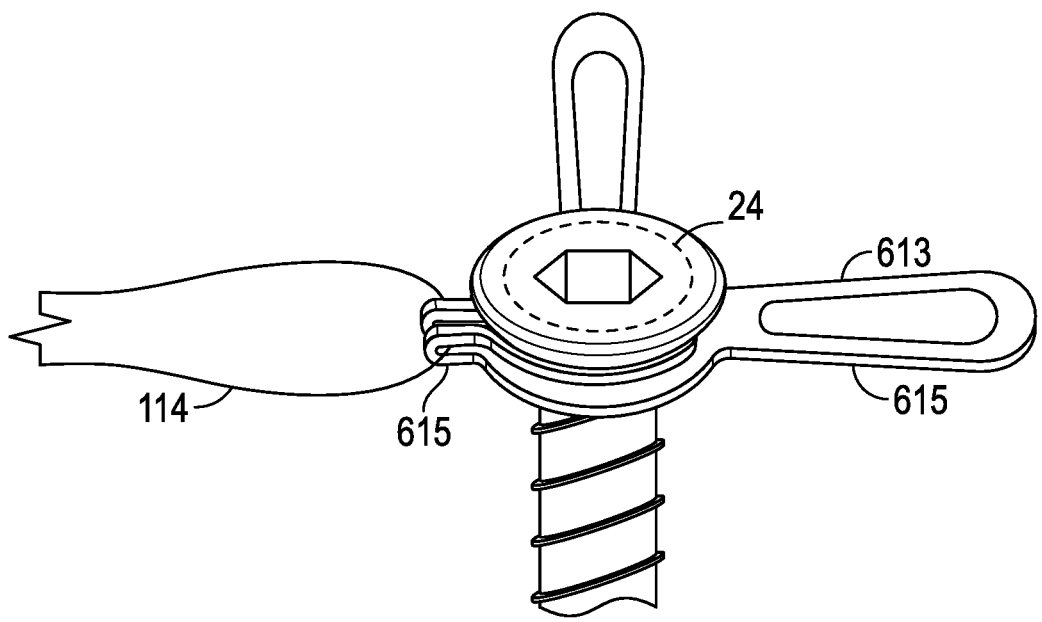
FIG. 19B is a perspective view of the suture coupling of FIG. 19A shown in a closed position.

In another version illustrated in FIGS. 19A and 19B, a suture coupling 613 may have a plurality of outwardly extending loops 615 and a screw receiving aperture 617. The suture coupling 613 is constructed of a flexible material. The outwardly extending loops 615 may be folded over the loop of a suture assembly, such as suture assembly 114, and in turn secured to a medial portion of the suture coupling 613 with a screw 24 inserted through the screw receiving aperture 617.

Figure 20:
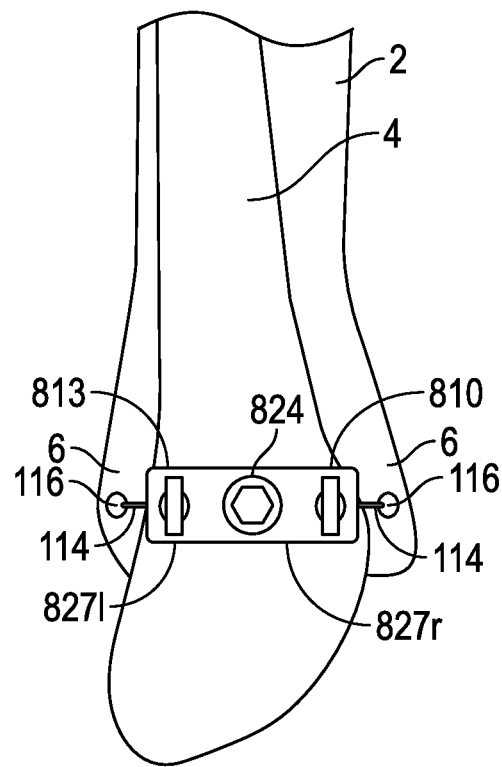
FIG. 20 is a lateral view of a portion of a tibia and fibula showing another embodiment of a fibula band assembly positioned to stabilize and reduce the fibula relative to the tibia.
Figure 21A:
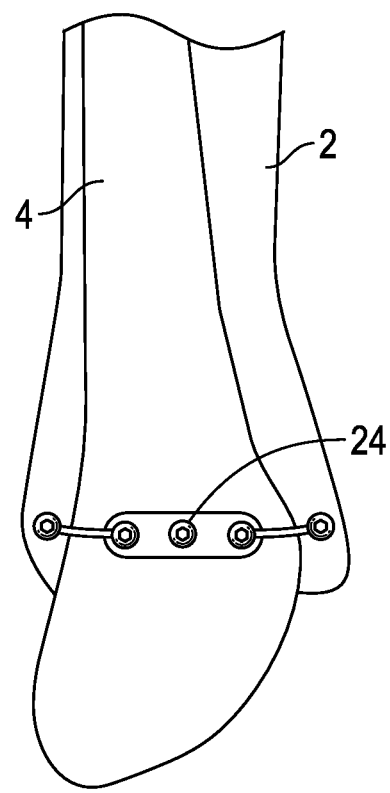
FIG. 21A is a lateral view of a portion of a tibia and fibula showing another embodiment of a fibula band assembly positioned to stabilize and reduce the fibula relative to the tibia.
Figure 21B:
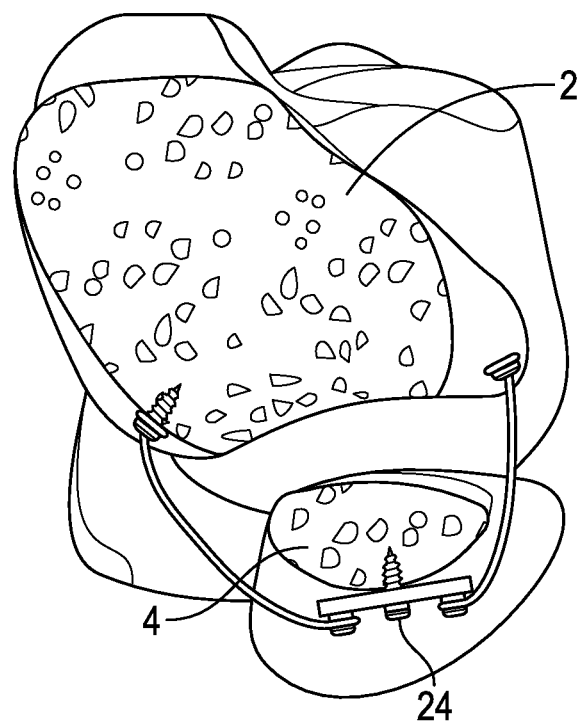
FIG. 21B is an axial view of the fibula band assembly of FIG. 21A.
Figure 22A:
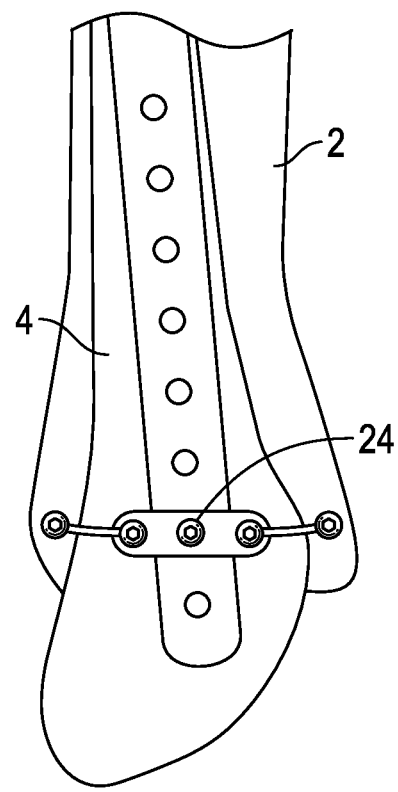
FIG. 22A is a lateral view of a portion of a tibia and fibula showing another embodiment of a fibula band assembly positioned to stabilize and reduce the fibula relative to the tibia.
Figure 22B:
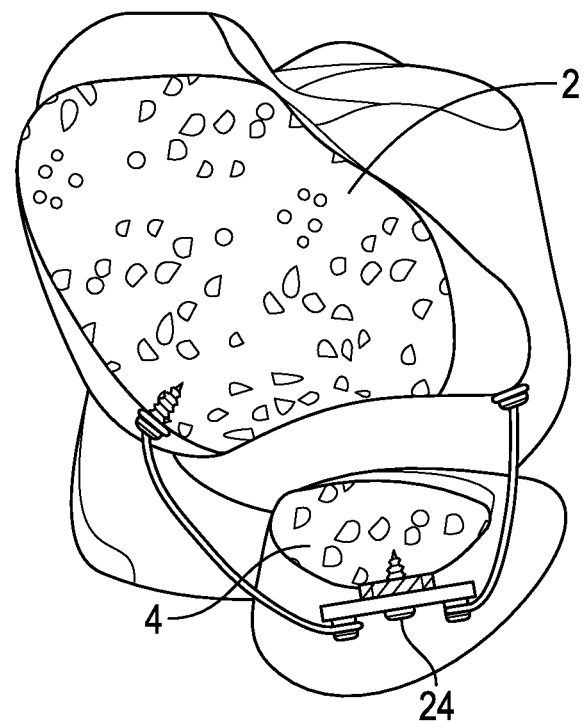
FIG. 22B is an axial view of the fibula band assembly of FIG. 22A.
Figure 23A:
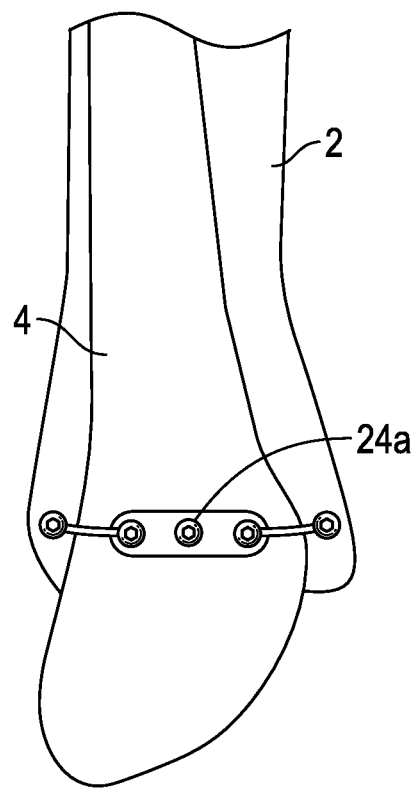
FIG. 23A is a lateral view of a portion of a tibia and fibula showing another embodiment of a fibula band assembly positioned to stabilize and reduce the fibula relative to the tibia.
Figure 23B:
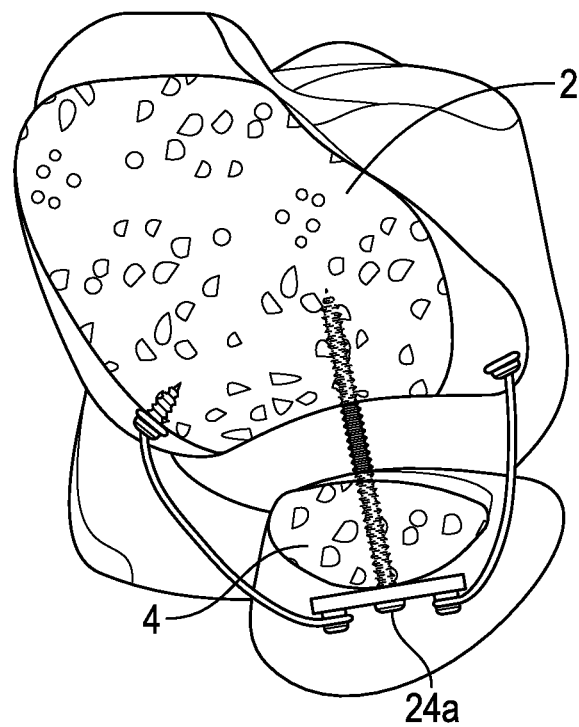
FIG. 23B is an axial view of the fibula band assembly of FIG. 23A.
Figure 24A:
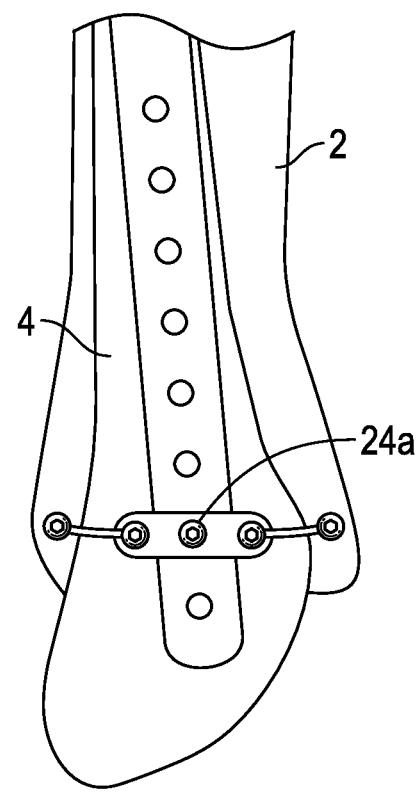
FIG. 24A is a lateral view of a portion of a tibia and fibula showing another embodiment of a fibula band assembly positioned to stabilize and reduce the fibula relative to the tibia.
Figure 24B:
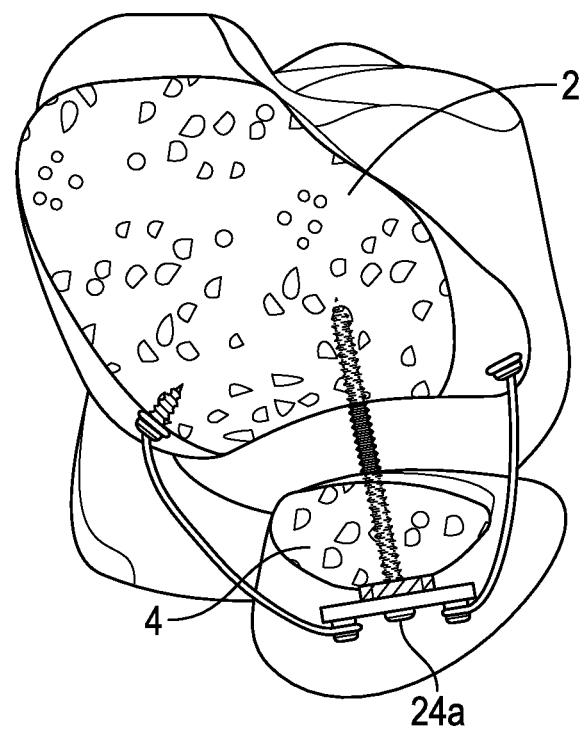
FIG. 24B is an axial view of the fibula band assembly of FIG. 24A.
Figure 25A:
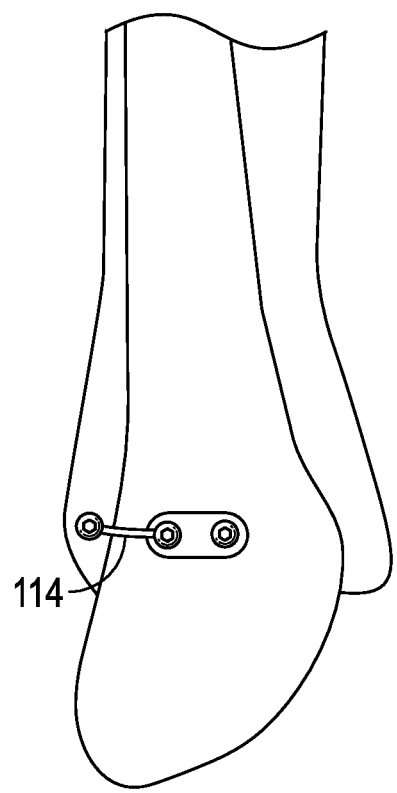
FIG. 25A is a lateral view of a portion of a tibia and fibula showing another embodiment of a fibula band assembly positioned to stabilize and reduce the fibula relative to the tibia.
Figure 25B:
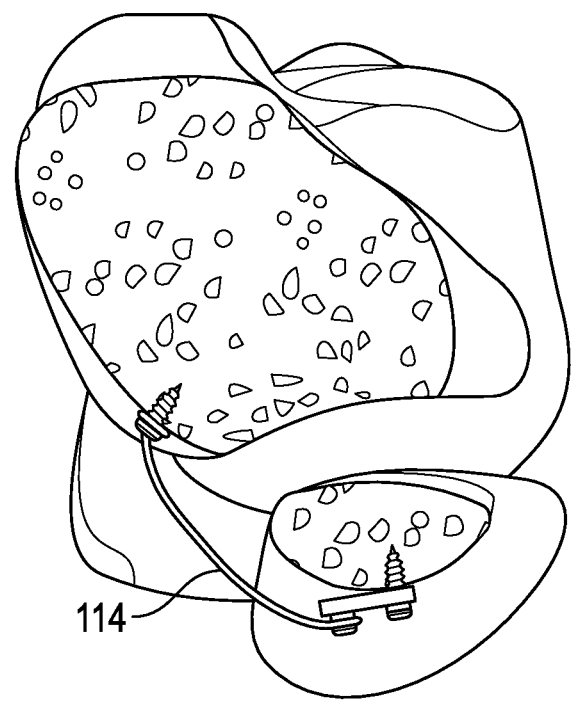
FIG. 25B is an axial view of the fibula band assembly of FIG. 25A.
Figure 26A:
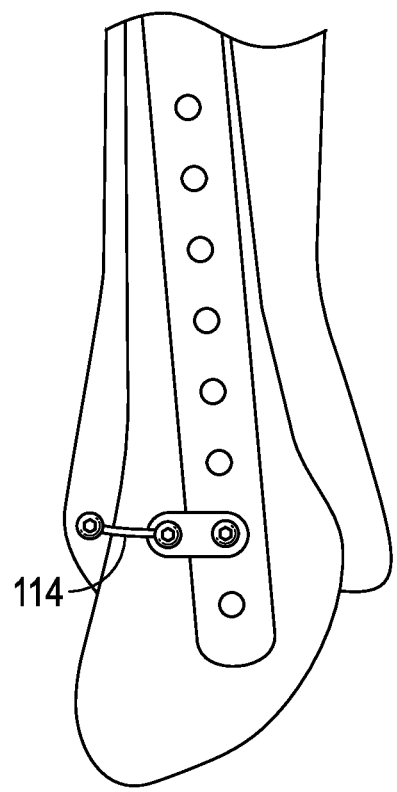
FIG. 26A is a lateral view of a portion of a tibia and fibula showing another embodiment of a fibula band assembly positioned to stabilize and reduce the fibula relative to the tibia.
Figure 26B:
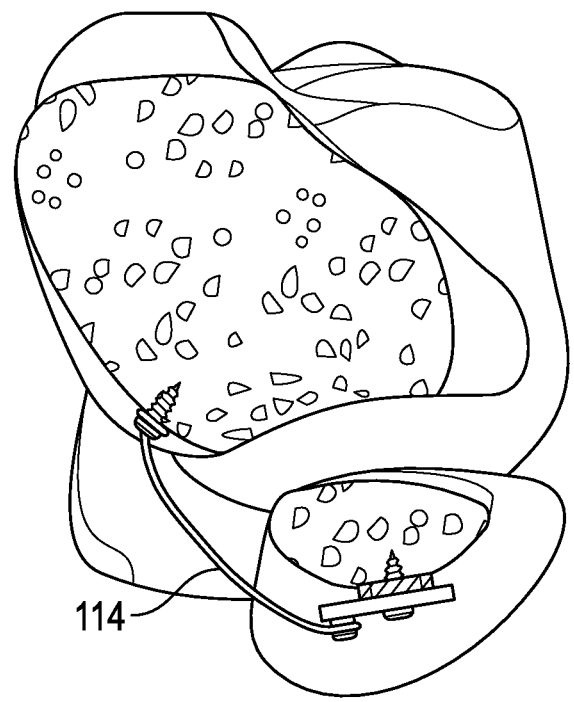
FIG. 26B is an axial view of the fibula band assembly of FIG. 26A.
Figure 27A:
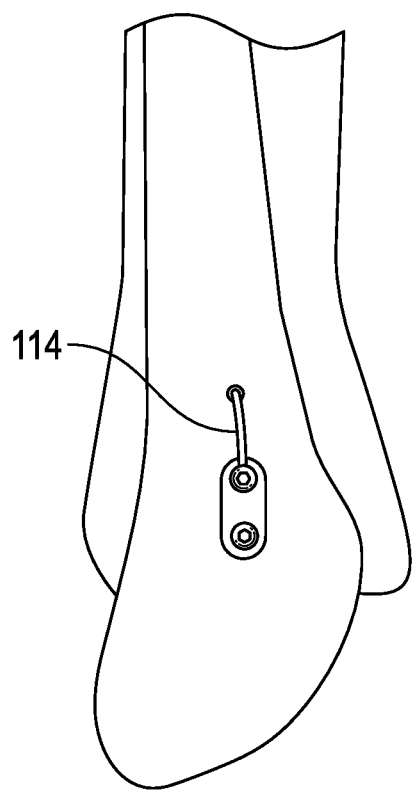
FIG. 27A is a lateral view of a portion of a tibia and fibula showing another embodiment of a fibula band assembly positioned to stabilize and reduce the fibula relative to the tibia.
Figure 27B:
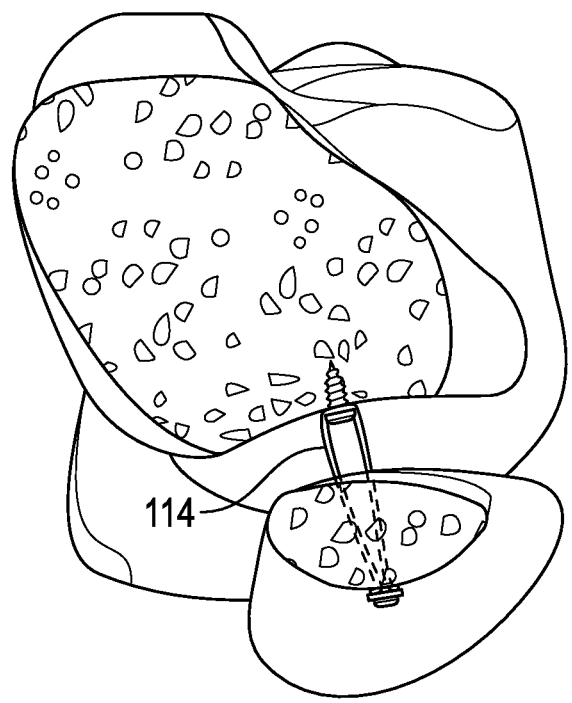
FIG. 27B is an axial view of the fibula band assembly of FIG. 27A.
Figure 28A:
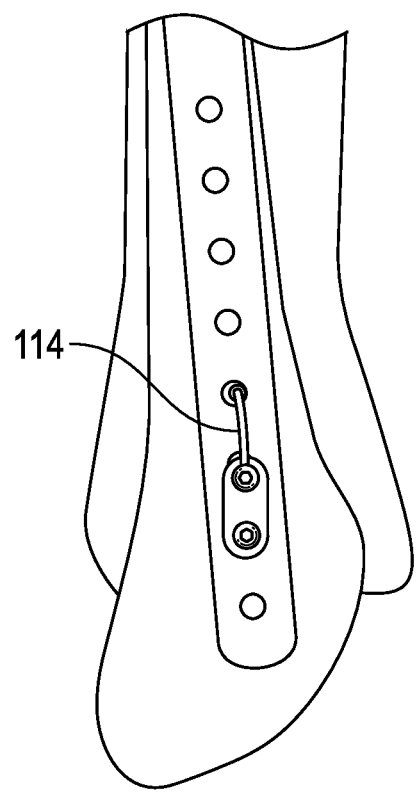
FIG. 28A is a lateral view of a portion of a tibia and fibula showing another embodiment of a fibula band assembly positioned to stabilize and reduce the fibula relative to the tibia.
Figure 28B:
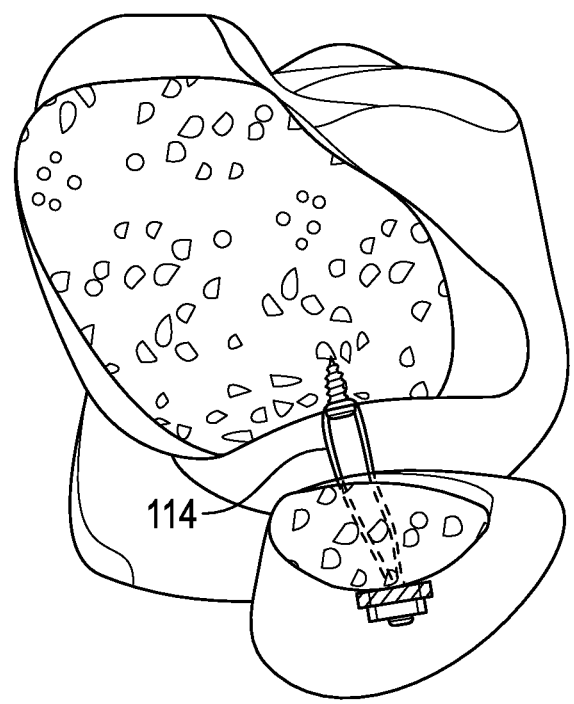
FIG. 28B is an axial view of the fibula band assembly of FIG. 28A.
Figure 29A:
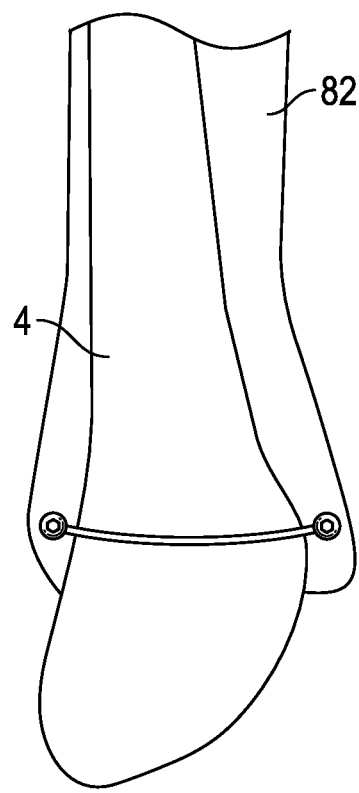
FIG. 29A is a lateral view of a portion of a tibia and fibula showing another embodiment of a fibula band assembly positioned to stabilize and reduce the fibula relative to the tibia.
Figure 29B:
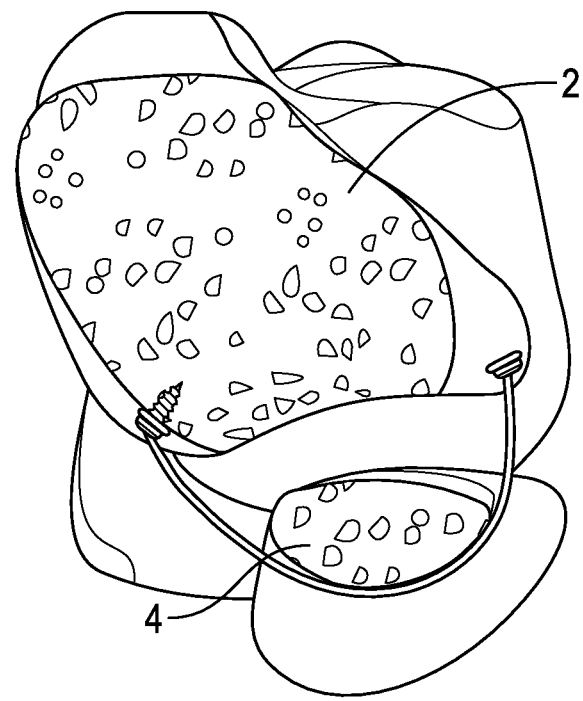
FIG. 29B is an axial view of the fibula band assembly of FIG. 29A.
Figure 30A:
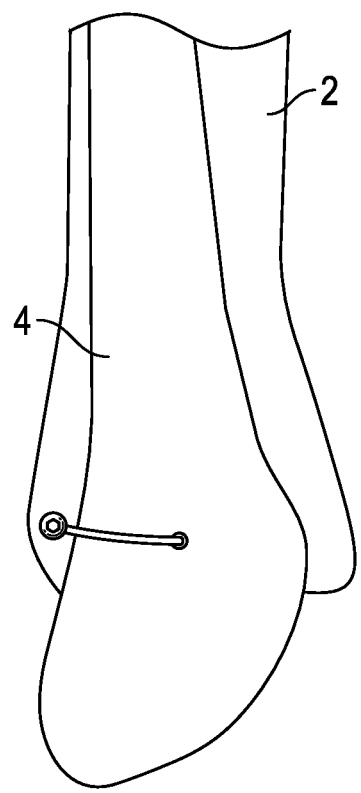
FIG. 30A is a lateral view of a portion of a tibia and fibula showing another embodiment of a fibula band assembly positioned to stabilize and reduce the fibula relative to the tibia.
Figure 30B:
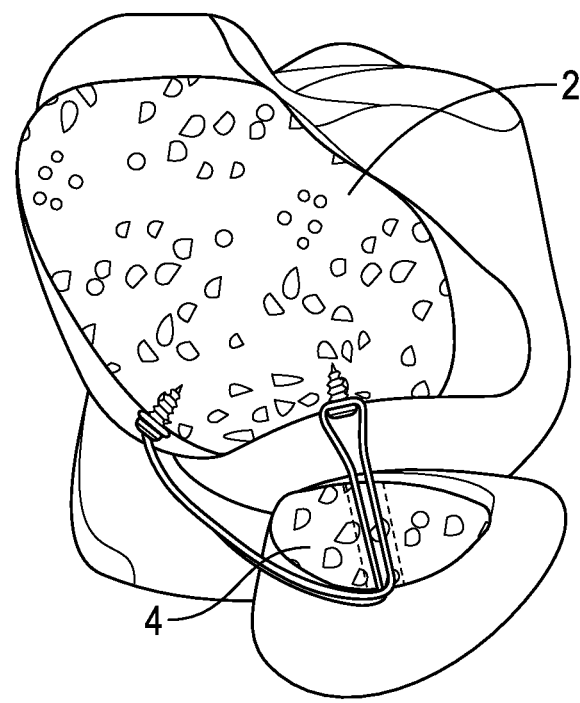
FIG. 30B is an axial view of the fibula band assembly of FIG. 30A.
Figure 31A:
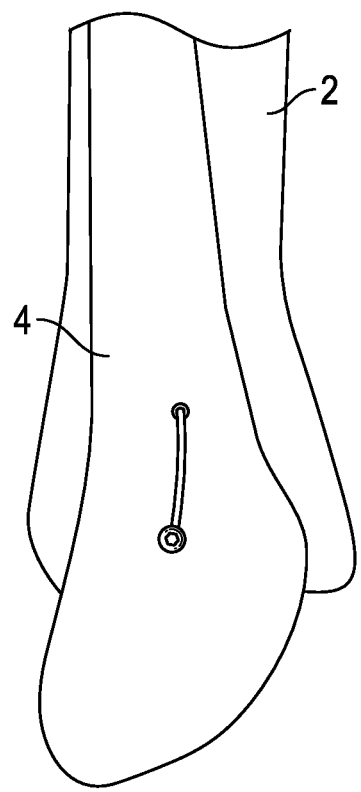
FIG. 31A is a lateral view of a portion of a tibia and fibula showing another embodiment of a fibula band assembly positioned to stabilize and reduce the fibula relative to the tibia.
Figure 31B:
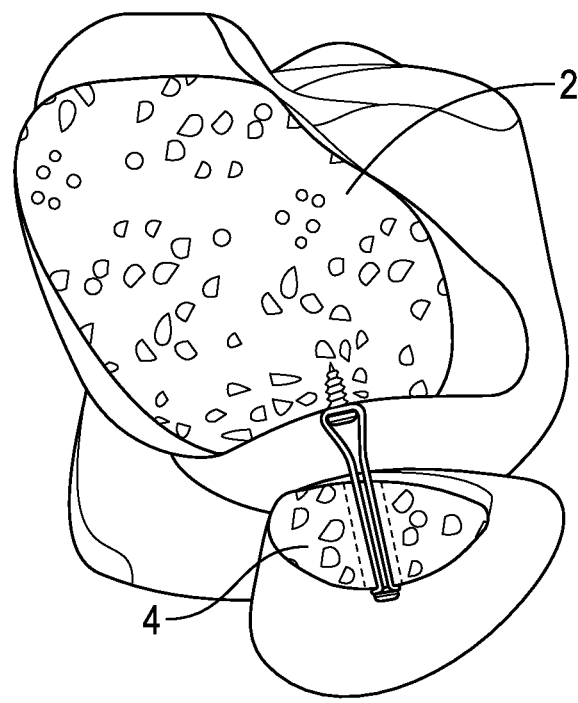
FIG. 31B is an axial view of the fibula band assembly of FIG. 31A.
Figure 32A:
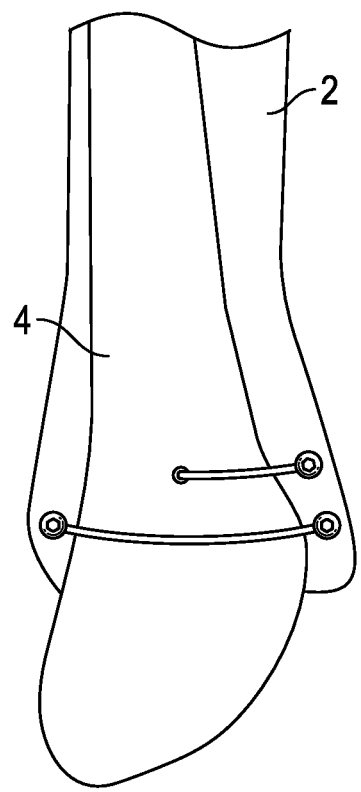
FIG. 32A is a lateral view of a portion of a tibia and fibula showing another embodiment of a fibula band assembly positioned to stabilize and reduce the fibula relative to the tibia.
Figure 32B:
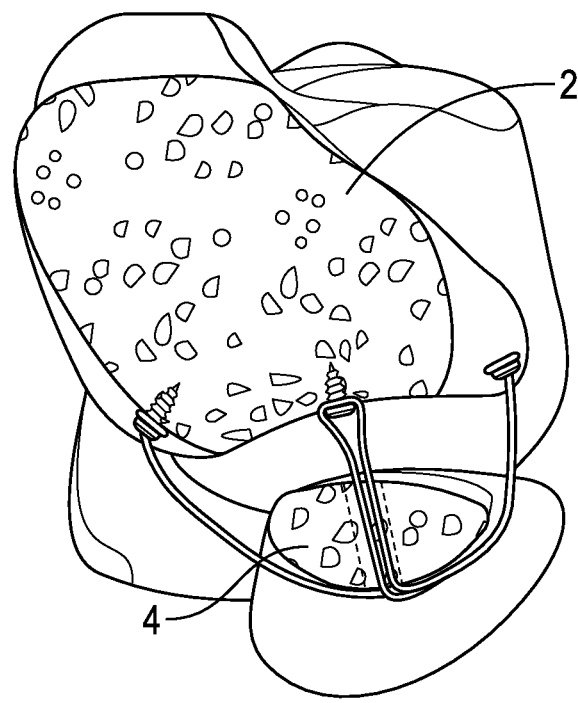
FIG. 32B is an axial view of the fibula band assembly of FIG. 32A.
Figure 33A:
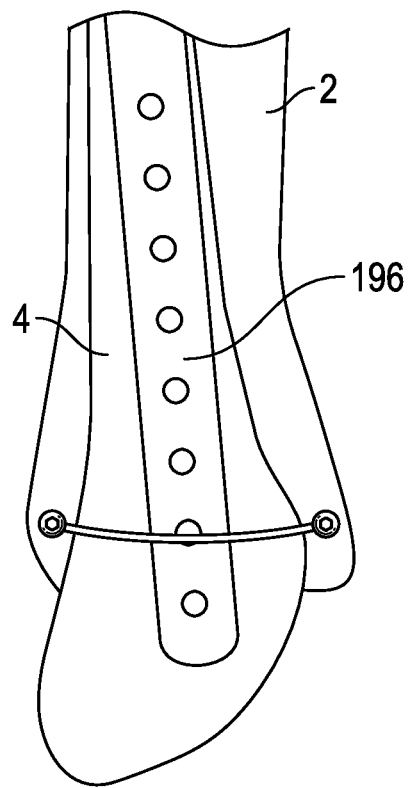
FIG. 33A is a lateral view of a portion of a tibia and fibula showing another embodiment of a fibula band assembly positioned to stabilize and reduce the fibula relative to the tibia.
Figure 33B:
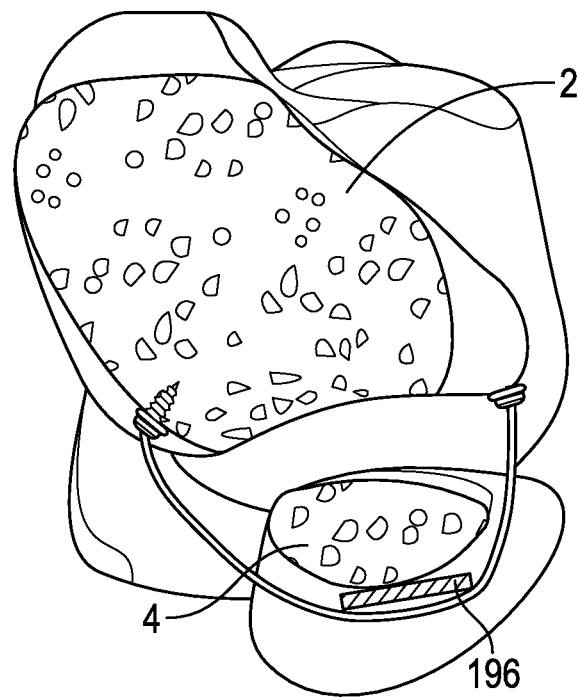
FIG. 33B is an axial view of the fibula band assembly of FIG. 33A.
Figure 34A:
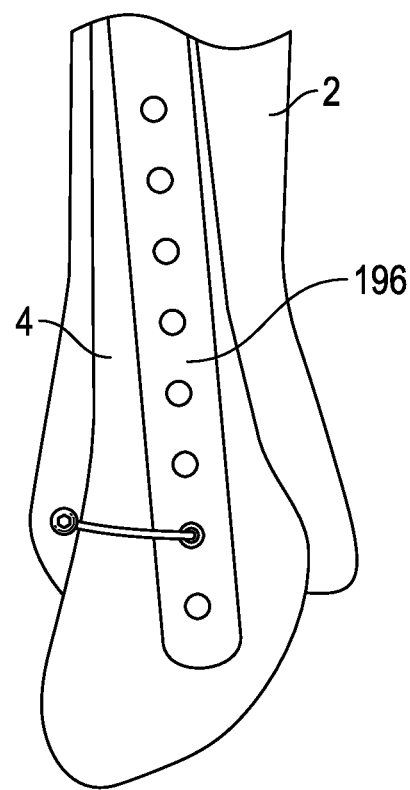
FIG. 34A is a lateral view of a portion of a tibia and fibula showing another embodiment of a fibula band assembly positioned to stabilize and reduce the fibula relative to the tibia.
Figure 34B:
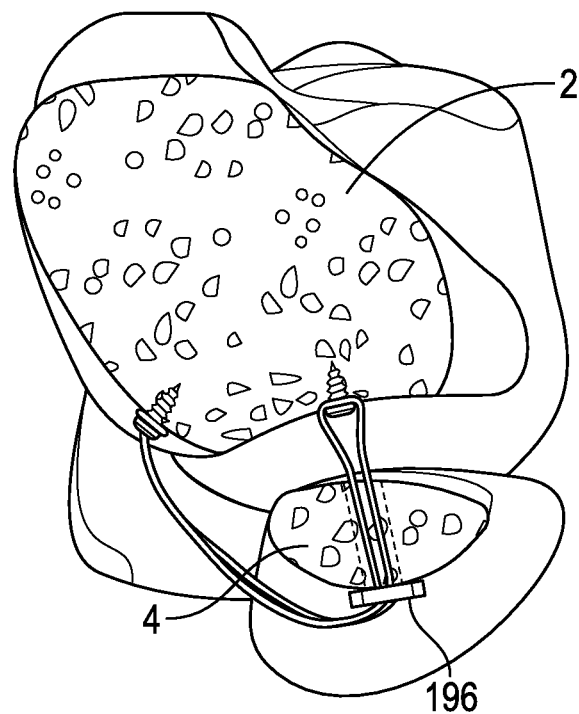
FIG. 34B is an axial view of the fibula band assembly of FIG. 34A.
Figure 35A:
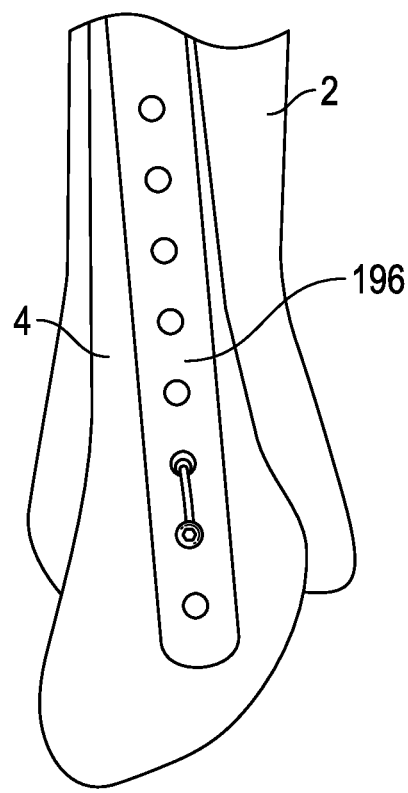
FIG. 35A is a lateral view of a portion of a tibia and fibula showing another embodiment of a fibula band assembly positioned to stabilize and reduce the fibula relative to the tibia.
Figure 35B:
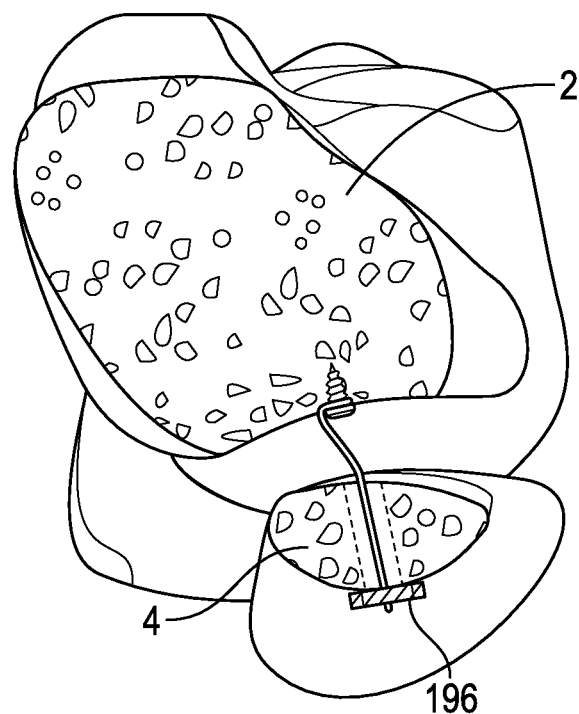
FIG. 35B is an axial view of the fibula band assembly of FIG. 35A.
Figure 36A:
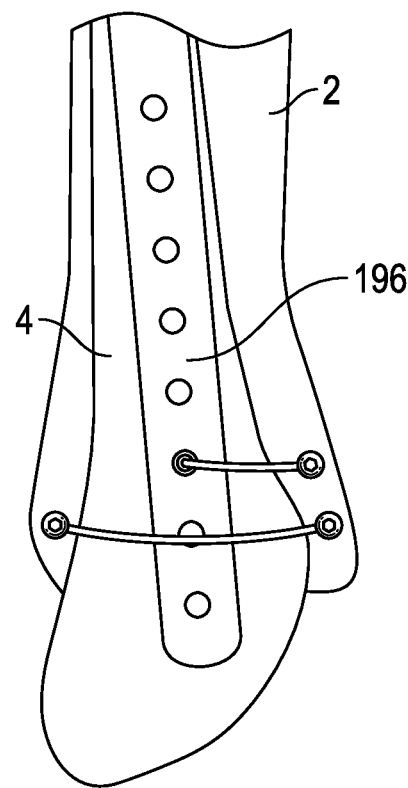
FIG. 36A is a lateral view of a portion of a tibia and fibula showing another embodiment of a fibula band assembly positioned to stabilize and reduce the fibula relative to the tibia.
Figure 36B:
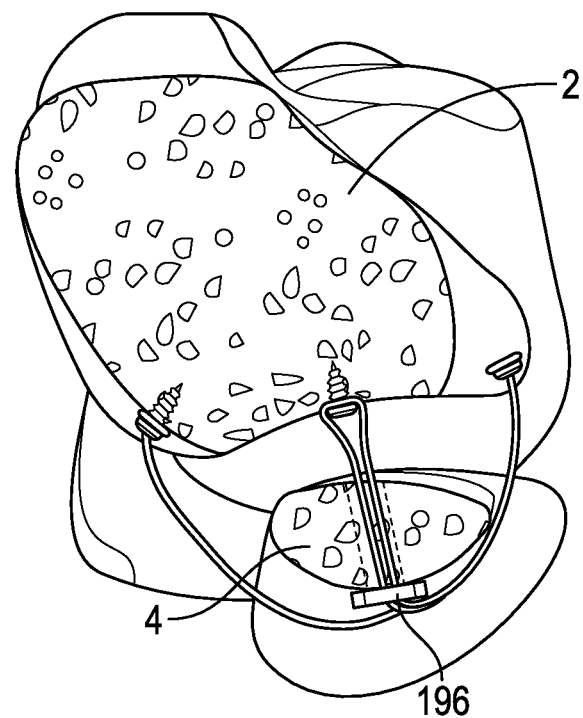
FIG. 36B is an axial view of the fibula band assembly of FIG. 36A.

With reference to FIG. 20, a fibula band assembly 810 with a suture coupling 813 constructed with two appendages 827-*l* and 827-*r* is shown. The fibula band 810 is shown attached to the tibia at the tubercules 6 of the tibia with two suture anchors 116. Additionally, the two suture anchors 116 are each attached to a suture assembly 114 that is threaded through the suture coupling 813 and secured by pulling the suture assembly 114 until the appropriate tension and reduction of the fibula 4 is complete. The suture coupling 813 additionally includes a screw aperture for receiving a fibula screw 824, which extends into the fibula to further secure the suture coupling 813. Additional embodiments include varied lengths of the fibula screw 824 or tibia/fibula screw based on the needs of the procedure and as previously described. The fibula screw 824 and/or tibia/fibula screws are meant to be removed later through a percutaneous approach if lateral stability is needed but rotational superior-inferior stability is not.

FIGS. 21-28 illustrate several exemplary arrangements for use of a screw to fix a suture coupling to the fibula. In particular, a screw 24 (FIGS. 21A, 21B, 22A, and 22B) may be employed which is sized such that it is just long enough to secure the suture coupling onto the fibula 4 wherein the screw threads reside within the internal bone of the fibula 4. Alternatively, the suture coupling may be fixed with a screw 24a (FIGS. 23A, 23B, 24A, and 24B) sized to extend through the fibula 4 and into the tibia 2 in order to fixate the fibula 4 within the fibular notch 8.

In addition to adding more fixation points, if a screw is incorporated into the construct, less fixation points (e.g., one) may be used depending on the number of ligaments that are damaged. For example, FIGS. 25-28 illustrate examples of using only one suture assembly 114. It will be appreciated that it may be desirable to utilize one suture assembly 114 in situations where only one ligament is disrupted.

FIGS. 29-36 illustrate additional configurations in which fibula band assemblies contemplated herein may be arranged. The suture anchors are placed in the medial side of the tibia. The suture assembly or suture assemblies may be arranged to extend about the fibula, as described above, or the suture assemblies may be arranged to pass through the fibula along one vector and around the fibula along a second vector. Also, multiple suture assemblies in multiple configurations may be employed. FIGS. 33-36 illustrate the arrangements shown in FIGS. 29-32, respectively, except in combination with a fracture plate, such as the fracture plate 196.

An exemplary method of implementing the fibula band assembly 110, with the suture coupling 113a shown in FIG. 5 being used as the example, will now be described.

An anchor hole may be drilled into the tibia 2 near the tubercles 6 of the tibia. A second anchor hole may be formed in the opposite tubercles of the tibia. The anchor holes are approximately 2.5 millimeters, by way of example. A suture anchor 16 is inserted into the anterior tubercle 6a with any suitable inserter tool. The inserter tool is removed from the suture anchor 16 leaving the exposed suture assembly. The same insertion procedures may be repeated on the posterior tubercle 6b.

After the suture anchors 16 are placed, a hole may be drilled in the fibula along the joint line. The hole may be drilled in a plate hole, if a bone plate is being employed on the fibula. The suture coupling 113a may be secured with a screw. In alternative embodiments, the suture coupling 113a may remain unfixed without a fibula screw, may be sandwiched between the bone plate and the bone, or may be placed over the plate as in the present description. When the suture coupling 1013 is not fixed in place, the tension of the suture assembly on the suture coupling 113a provides the necessary force to fix the suture coupling in a desired position.

The suture assemblies 114 may then be threaded through the suture coupling 113a with the toggle anchors 128 being pulled from the anterior and posterior anchors through the suture coupling 113a in their respective apertures. The threading strands may then be removed from the toggle anchors 128, and the suture assembles 114 tensioned to stabilize and reduce the fibula relative to the tibia. Finally, with the suture assemblies 114 in a tensioned condition, the setting strands may be trimmed.

From the above description, it is clear that the inventive concepts disclosed and claimed herein are well adapted to carry out the objects and to attain the advantages mentioned herein, as well as those inherent in the invention. While exemplary embodiments of the inventive concepts have been described for purposes of this disclosure, it will be understood that numerous changes may be made which will readily suggest them to those skilled in the art and which are accomplished within the spirit of the inventive concepts disclosed and/or as defined in the appended claims.

What is claimed is:

1. A method for syndesmosis fixation, comprising:
attaching a first suture anchor to a first tubercle of a tibia;
attaching a second suture anchor to second tubercle of the tibia so that the first suture anchor and the second suture anchor are positioned on opposing sides of a fibular notch of the tibia;
extending a first suture assembly around a portion of a fibula from the first suture anchor to a suture coupling;
extending a second suture assembly around another portion of the fibula from the second suture anchor to the suture coupling; and
tensioning at least one of the first and second suture assemblies to stabilize and reduce the fibula relative to the tibia.

2. The method of claim 1, further comprising conforming the suture coupling to the contour of a surface of the fibula.

3. The method of claim 1, further comprising tensioning the first suture assembly and the second suture assembly to stabilize and reduce the fibula relative to the tibia.

4. The method of claim 1, wherein the step of extending the first suture assembly around a portion of the fibula from the first suture anchor to the suture coupling includes attaching a first loop of the first suture assembly to the first suture anchor and attaching a second loop of the first suture assembly to the suture coupling.

5. The method of claim 4, wherein the step of extending the second suture assembly around a portion of the fibula from the second suture anchor to the suture coupling includes attaching a first loop of the second suture assembly to the second suture anchor and attaching a second loop of the second suture assembly to the suture coupling.

6. The method of claim 5, further comprising tensioning the first suture assembly and the second suture assembly to stabilize and reduce the fibula relative to the tibia.

7. The method of claim 1, further comprising:
attaching a third suture anchor to the tibia; and
extending a third suture assembly through the fibula from the third suture anchor to the suture coupling.

8. The method of claim 7, further comprising:
tensioning the first suture assembly, the second suture assembly, and the third suture assembly to stabilize and reduce the fibula relative to the tibia.

9. The method of claim 7, further comprising:
extending the first suture assembly to a first appendage of the suture coupling;
extending the second suture assembly to a second appendage of the suture coupling; and
extending the third suture assembly to a third appendage of the suture coupling.

* * * * *